US011771439B2

(12) United States Patent
Miller et al.

(10) Patent No.: US 11,771,439 B2
(45) Date of Patent: Oct. 3, 2023

(54) POWERED DRIVER

(71) Applicant: TELEFLEX LIFE SCIENCES LIMITED, Valletta (MT)

(72) Inventors: Larry J. Miller, Spring Branch, TX (US); David S. Bolleter, San Antonio, TX (US); Robert W. Titkemeyer, San Antonio, TX (US); Christopher B. Kilcoin, Santa Cruz, CA (US); Matthew T. Harmon, Santa Cruz, CA (US); Ruben Trevino, San Antonio, TX (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 222 days.

(21) Appl. No.: 16/105,541

(22) Filed: Aug. 20, 2018

(65) Prior Publication Data

US 2018/0353191 A1    Dec. 13, 2018

Related U.S. Application Data

(60) Continuation of application No. 13/609,001, filed on Sep. 10, 2012, now Pat. No. 10,052,111, which is a
(Continued)

(51) Int. Cl.
*A61B 17/16*   (2006.01)
*A61B 10/02*   (2006.01)
(Continued)

(52) U.S. Cl.
CPC ............ *A61B 17/16* (2013.01); *A61B 10/025* (2013.01); *A61B 17/1622* (2013.01);
(Continued)

(58) Field of Classification Search
CPC ............ A61B 2010/0258; A61B 17/16; A61B 17/1622; A61B 17/3472; B23B 45/00
See application file for complete search history.

(56) References Cited

U.S. PATENT DOCUMENTS

| 1,272,104 A | 7/1918 | Riethmueller |
| 1,539,637 A | 5/1925 | Bronner |
(Continued)

FOREIGN PATENT DOCUMENTS

| CA | 2138842 A1 | 6/1996 |
| CA | 2366676 A1 | 9/2000 |
(Continued)

OTHER PUBLICATIONS

Australian Exam Report on Patent Application No. 2003240970, 2 pages, Oct. 15, 2007.
(Continued)

*Primary Examiner* — David W Bates
(74) *Attorney, Agent, or Firm* — BakerHostetler

(57) ABSTRACT

An apparatus and methods are provided to penetrate a bone and associated bone marrow using a powered driver having a gear assembly and a motor. The powered driver may include an indicator operable to show status of a power supply associated with the powered driver. The power supply may include a battery power pack having a diamond shaped cross section. The powered driver may have a handle with a corresponding cross section.

17 Claims, 5 Drawing Sheets

Related U.S. Application Data division of application No. 12/025,580, filed on Feb. 4, 2008, now Pat. No. 9,504,477.

(60) Provisional application No. 60/910,147, filed on Apr. 4, 2007.

(51) Int. Cl.
| | | |
|---|---|---|
| *A61B 17/34* | (2006.01) | |
| *F41A 17/54* | (2006.01) | |
| *F41A 17/46* | (2006.01) | |
| *F41A 17/52* | (2006.01) | |
| *B23B 45/00* | (2006.01) | |
| *A61B 17/32* | (2006.01) | |
| *B23B 45/02* | (2006.01) | |
| *B25B 23/12* | (2006.01) | |
| *B25B 23/00* | (2006.01) | |
| *A61B 90/11* | (2016.01) | |
| *A61B 17/3205* | (2006.01) | |
| *A61B 17/00* | (2006.01) | |

(52) U.S. Cl.
CPC .... *A61B 17/32002* (2013.01); *A61B 17/3476* (2013.01); *B23B 45/00* (2013.01); *B23B 45/02* (2013.01); *F41A 17/46* (2013.01); *F41A 17/52* (2013.01); *F41A 17/54* (2013.01); *A61B 17/1637* (2013.01); *A61B 17/32053* (2013.01); *A61B 17/3472* (2013.01); *A61B 90/11* (2016.02); *A61B 2010/0258* (2013.01); *A61B 2017/0046* (2013.01); *A61B 2017/00398* (2013.01); *A61B 2017/00734* (2013.01); *B25B 23/0035* (2013.01); *B25B 23/12* (2013.01); *B25D 2250/141* (2013.01)

(56) References Cited

U.S. PATENT DOCUMENTS

| | | | |
|---|---|---|---|
| 1,686,482 A | | 10/1928 | Windle |
| 1,954,620 A | | 4/1934 | Connell |
| 2,080,202 A | | 5/1937 | Drake |
| 2,130,845 A | | 9/1938 | Jurgen |
| 2,138,842 A | | 12/1938 | Drew |
| 2,219,605 A | | 10/1940 | Turkel |
| 2,261,958 A | | 11/1941 | Burri |
| 2,317,648 A | | 4/1943 | Siqveland |
| 2,318,648 A | | 5/1943 | Penfold |
| 2,419,045 A | | 4/1947 | Whittaker |
| 2,426,535 A | | 8/1947 | Turkel |
| 2,525,588 A | | 10/1950 | Cameron et al. |
| 2,525,839 A | * | 10/1950 | Sparklin ............... B23B 45/02 |
| | | | 173/170 |
| 2,590,516 A | | 3/1952 | De Von |
| 2,660,635 A | | 11/1953 | Wood |
| 2,714,026 A | * | 7/1955 | Schultz ................. B23Q 3/12 |
| | | | 403/183 |
| RE24,056 E | | 8/1955 | Johansen |
| 2,766,907 A | | 10/1956 | Wallace, Jr. |
| 2,773,501 A | | 12/1956 | Young |
| 2,817,648 A | | 12/1957 | Gould et al. |
| 2,860,635 A | | 11/1958 | Wilburn |
| 2,876,369 A | | 3/1959 | Otto |
| 3,022,596 A | | 2/1962 | Cannon |
| 3,104,448 A | | 9/1963 | Morrow |
| 3,120,845 A | | 2/1964 | Horner |
| 3,173,417 A | | 3/1965 | Horner |
| 3,175,554 A | | 3/1965 | Stewart |
| 3,269,046 A | | 8/1966 | Schaefer |
| 3,413,498 A | * | 11/1968 | Bowen, III ............ H02K 7/145 |
| | | | 310/47 |
| 3,507,276 A | | 4/1970 | Burgess |
| 3,519,858 A | * | 7/1970 | Morganson .......... B23B 45/008 |
| | | | 310/47 |
| 3,529,580 A | | 9/1970 | Stevens |
| 3,536,943 A | | 10/1970 | Bowen |
| 3,543,966 A | | 12/1970 | Ryan |
| 3,590,232 A | | 6/1971 | Sadowski |
| 3,598,108 A | | 8/1971 | Jamshidi et al. |
| 3,664,163 A | | 5/1972 | Foote |
| 3,671,699 A | | 6/1972 | Matthews |
| 3,697,223 A | | 10/1972 | Kovalcik et al. |
| 3,713,417 A | | 1/1973 | Shugart |
| 3,719,186 A | | 3/1973 | Merig |
| 3,734,207 A | * | 5/1973 | Fishbein ............. A61B 17/1622 |
| | | | 173/217 |
| 3,750,667 A | | 8/1973 | Pshenichny et al. |
| 3,802,555 A | | 4/1974 | Grasty et al. |
| 3,815,605 A | | 6/1974 | Schmidt et al. |
| 3,835,860 A | | 9/1974 | Garretson |
| 3,843,143 A | * | 10/1974 | Laxson ................... B23B 45/06 |
| | | | 279/144 |
| 3,844,291 A | | 10/1974 | Moen |
| 3,850,158 A | | 11/1974 | Elias et al. |
| 3,893,445 A | | 7/1975 | Hofsess |
| 3,893,455 A | | 7/1975 | McNally |
| 3,935,909 A | * | 2/1976 | Mabuchi ................. B23B 45/02 |
| | | | 173/217 |
| 3,976,066 A | | 8/1976 | McCartney |
| 3,981,398 A | | 9/1976 | Boshoff |
| 3,991,765 A | | 11/1976 | Cohen |
| 3,999,110 A | | 12/1976 | Ramstrom et al. |
| 4,021,920 A | | 5/1977 | Kirschner et al. |
| 4,040,462 A | | 8/1977 | Hattan |
| 4,046,254 A | | 9/1977 | Kramer |
| 4,099,518 A | | 7/1978 | Baylis et al. |
| 4,124,026 A | | 11/1978 | Berner et al. |
| 4,142,517 A | | 3/1979 | Contreras Guerrero de Stavropoulos et al. |
| 4,154,026 A | | 5/1979 | Palthe |
| 4,157,714 A | | 6/1979 | Foltz et al. |
| 4,170,993 A | | 10/1979 | Alvarez |
| 4,185,619 A | | 1/1980 | Reiss |
| 4,189,266 A | | 2/1980 | Koslow |
| 4,194,505 A | | 3/1980 | Schmitz |
| 4,200,111 A | | 4/1980 | Harris |
| 4,213,462 A | | 7/1980 | Sato |
| 4,258,722 A | | 3/1981 | Sessions et al. |
| 4,262,676 A | | 4/1981 | Jamshidi |
| 4,266,555 A | | 5/1981 | Jamshidi |
| 4,269,192 A | | 5/1981 | Matsuo |
| 4,299,230 A | | 11/1981 | Kubota |
| 4,306,570 A | | 12/1981 | Matthews |
| 4,316,463 A | | 2/1982 | Schmitz et al. |
| 4,330,093 A | | 5/1982 | Chapman, Jr. |
| 4,333,459 A | | 6/1982 | Becker |
| 4,334,529 A | | 6/1982 | Wirth |
| 4,356,826 A | | 11/1982 | Kubota |
| 4,359,052 A | | 11/1982 | Staub |
| 4,373,518 A | | 2/1983 | Kaiser et al. |
| 4,378,053 A | | 3/1983 | Simpson |
| 4,381,777 A | | 5/1983 | Garnier |
| 4,393,872 A | | 7/1983 | Reznik et al. |
| 4,399,723 A | | 8/1983 | Marleau |
| 4,413,760 A | | 11/1983 | Paton |
| 4,416,503 A | | 11/1983 | Hayes |
| 4,420,085 A | | 12/1983 | Wilson et al. |
| 4,431,006 A | | 2/1984 | Trimmer et al. |
| 4,441,563 A | | 4/1984 | Walton, II |
| 4,461,305 A | | 7/1984 | Cibley |
| 4,469,109 A | | 9/1984 | Mehl |
| 4,484,577 A | | 11/1984 | Sackner et al. |
| 4,487,209 A | | 12/1984 | Mehl |
| 4,504,267 A | | 3/1985 | Parmelee et al. |
| 4,522,302 A | | 6/1985 | Paikoff |
| 4,543,966 A | | 10/1985 | Islam et al. |
| 4,553,539 A | | 11/1985 | Morris |
| 4,578,064 A | | 3/1986 | Sarnoff et al. |
| 4,595,322 A | | 6/1986 | Clement |
| 4,605,011 A | | 8/1986 | Naslund |
| 4,620,539 A | | 11/1986 | Andrews et al. |
| 4,623,335 A | | 11/1986 | Jackson |
| 4,630,616 A | | 12/1986 | Tretinyak |

(56) References Cited

U.S. PATENT DOCUMENTS

| | | |
|---|---|---|
| 4,645,492 A | 2/1987 | Weeks |
| 4,646,731 A | 3/1987 | Brower |
| 4,654,030 A | 3/1987 | Moll et al. |
| 4,654,492 A | 3/1987 | Koerner et al. |
| 4,655,226 A | 4/1987 | Lee |
| 4,659,329 A | 4/1987 | Annis |
| 4,670,008 A | 6/1987 | Von Albertini |
| 4,671,292 A | 6/1987 | Matzuk |
| 4,691,929 A | 9/1987 | Neumaier et al. |
| 4,692,073 A | 9/1987 | Martindell |
| 4,696,308 A | 9/1987 | Meller et al. |
| 4,702,261 A | 10/1987 | Cornell et al. |
| 4,711,636 A | 12/1987 | Bierman |
| 4,713,061 A | 12/1987 | Tarello et al. |
| 4,716,901 A | 1/1988 | Jackson et al. |
| 4,720,881 A | 1/1988 | Meyers |
| 4,723,945 A | 2/1988 | Theiling |
| 4,728,876 A | 3/1988 | Mongeon et al. |
| 4,736,850 A | 4/1988 | Bowman et al. |
| 4,753,345 A | 6/1988 | Goodsir et al. |
| 4,758,225 A | 7/1988 | Cox et al. |
| 4,762,118 A | 8/1988 | Lia et al. |
| 4,772,261 A | 9/1988 | Von Hoff et al. |
| 4,787,893 A | 11/1988 | Villette |
| 4,793,363 A | 12/1988 | Ausherman et al. |
| 4,801,293 A | 1/1989 | Jackson |
| 4,810,248 A | 3/1989 | Masters et al. |
| 4,812,008 A | 3/1989 | Tokumaru et al. |
| 4,838,282 A | 6/1989 | Strasser et al. |
| 4,838,877 A | 6/1989 | Massau |
| 4,844,259 A | 7/1989 | Glowczewskie, Jr. et al. |
| 4,867,158 A | 9/1989 | Sugg |
| 4,874,181 A * | 10/1989 | Hsu .............. B23B 51/12 279/144 |
| 4,883,470 A | 11/1989 | Haindl |
| 4,919,146 A | 4/1990 | Rhinehart et al. |
| 4,919,653 A | 4/1990 | Martinez et al. |
| 4,921,013 A | 5/1990 | Spalink et al. |
| 4,922,602 A | 5/1990 | Mehl |
| 4,935,010 A | 6/1990 | Cox et al. |
| 4,940,459 A | 7/1990 | Noce |
| 4,944,677 A | 7/1990 | Alexandre |
| 4,969,870 A | 11/1990 | Kramer et al. |
| 4,976,269 A | 12/1990 | Mehl |
| 4,986,279 A | 1/1991 | ONeill |
| 5,002,546 A | 3/1991 | Romano |
| 5,012,605 A | 5/1991 | Nishioka |
| 5,025,797 A | 6/1991 | Baran |
| 5,036,860 A | 8/1991 | Leigh et al. |
| 5,040,542 A | 8/1991 | Gray |
| 5,057,085 A | 10/1991 | Kopans |
| 5,064,426 A | 11/1991 | Huebsch |
| 5,074,311 A | 12/1991 | Hasson |
| 5,075,994 A | 12/1991 | Nishioka |
| 5,104,382 A | 4/1992 | Brinkerhoff et al. |
| 5,116,324 A | 5/1992 | Brierley et al. |
| 5,120,312 A | 6/1992 | Wigness et al. |
| 5,122,114 A | 6/1992 | Miller et al. |
| 5,133,359 A | 7/1992 | Kedem |
| 5,137,500 A | 8/1992 | Lhotak |
| 5,137,518 A | 8/1992 | Mersch |
| 5,139,500 A | 8/1992 | Schwartz |
| RE34,056 E | 9/1992 | Lindgren et al. |
| 5,145,369 A | 9/1992 | Lustig et al. |
| 5,148,813 A | 9/1992 | Bucalo |
| 5,156,399 A | 10/1992 | Gauer |
| 5,159,163 A | 10/1992 | Bahjat et al. |
| 5,172,700 A | 12/1992 | Bencini et al. |
| 5,172,701 A | 12/1992 | Leigh |
| 5,172,702 A | 12/1992 | Leigh et al. |
| 5,176,415 A | 1/1993 | Choksi |
| 5,176,643 A | 1/1993 | Kramer et al. |
| 5,183,054 A | 2/1993 | Burkholder et al. |
| 5,184,611 A | 2/1993 | Turnbull |
| 5,187,422 A | 2/1993 | Izenbaard et al. |
| 5,195,985 A | 3/1993 | Hall |
| 5,203,056 A | 4/1993 | Funk et al. |
| 5,204,670 A | 4/1993 | Stinton |
| 5,207,303 A | 5/1993 | Oswalt et al. |
| 5,207,697 A * | 5/1993 | Carusillo .......... A61B 17/1626 320/115 |
| 5,209,721 A | 5/1993 | Wilk |
| 5,210,376 A | 5/1993 | Caviar |
| 5,217,478 A | 6/1993 | Rexroth |
| D338,270 S | 8/1993 | Stephens et al. |
| 5,235,981 A | 8/1993 | Hascoet et al. |
| 5,244,619 A | 9/1993 | Burnham |
| 5,249,583 A | 10/1993 | Mallaby |
| 5,257,632 A | 11/1993 | Turkel et al. |
| 5,257,972 A | 11/1993 | Gurmarnik |
| 5,261,877 A | 11/1993 | Fine et al. |
| 5,261,891 A | 11/1993 | Brinkerhoff et al. |
| 5,269,785 A | 12/1993 | Bonutti |
| 5,271,380 A | 12/1993 | Riek et al. |
| 5,271,414 A | 12/1993 | Partika et al. |
| 5,271,744 A | 12/1993 | Kramer et al. |
| 5,279,306 A | 1/1994 | Mehl |
| 5,300,070 A | 4/1994 | Gentelia et al. |
| 5,312,351 A | 5/1994 | Gerrone |
| 5,312,361 A | 5/1994 | Zadini et al. |
| 5,312,364 A | 5/1994 | Jacobs |
| 5,312,408 A | 5/1994 | Brown |
| 5,313,733 A | 5/1994 | Meade |
| 5,315,737 A | 5/1994 | Ouimet |
| 5,318,543 A | 6/1994 | Ross et al. |
| 5,318,589 A | 6/1994 | Lichtman |
| 5,320,110 A | 6/1994 | Wang |
| 5,324,300 A | 6/1994 | Elias et al. |
| 5,330,480 A | 7/1994 | Meloul et al. |
| 5,331,972 A | 7/1994 | Wadhwani et al. |
| 5,332,398 A | 7/1994 | Miller et al. |
| 5,333,790 A | 8/1994 | Christopher |
| 5,334,169 A | 8/1994 | Brown et al. |
| 5,334,204 A | 8/1994 | Clewett et al. |
| 5,339,831 A | 8/1994 | Thompson |
| 5,341,316 A | 8/1994 | Nishigaki |
| 5,341,816 A | 8/1994 | Allen |
| 5,341,823 A | 8/1994 | Manosalva et al. |
| 5,344,420 A | 9/1994 | Hilal et al. |
| 5,348,022 A | 9/1994 | Leigh et al. |
| 5,354,287 A | 10/1994 | Wacks |
| 5,356,006 A | 10/1994 | Alpern et al. |
| 5,357,974 A | 10/1994 | Baldridge |
| 5,357,979 A | 10/1994 | Imran |
| 5,361,853 A * | 11/1994 | Takamura ............ B25B 21/00 173/117 |
| 5,366,445 A | 11/1994 | Haber et al. |
| 5,368,046 A | 11/1994 | Scarfone et al. |
| 5,372,583 A | 12/1994 | Roberts et al. |
| 5,383,859 A | 1/1995 | Sewell, Jr. |
| 5,385,151 A | 1/1995 | Scarfone et al. |
| 5,385,553 A | 1/1995 | Hart et al. |
| 5,389,553 A | 2/1995 | Grubisich et al. |
| 5,394,875 A | 3/1995 | Lewis et al. |
| 5,400,798 A | 3/1995 | Baran |
| 5,405,348 A | 4/1995 | Anspach, Jr. et al. |
| 5,405,362 A | 4/1995 | Kramer et al. |
| 5,407,243 A | 4/1995 | Riemann |
| 5,421,821 A | 6/1995 | Janicki et al. |
| 5,423,796 A | 6/1995 | Shikhman et al. |
| 5,423,824 A | 6/1995 | Akerfeldt et al. |
| 5,431,151 A | 7/1995 | Riek et al. |
| 5,431,655 A | 7/1995 | Melker et al. |
| 5,432,459 A | 7/1995 | Thompson et al. |
| 5,436,566 A | 7/1995 | Thompson et al. |
| 5,437,119 A | 8/1995 | Womack |
| 5,449,370 A | 9/1995 | Vaitekunas |
| 5,451,210 A | 9/1995 | Kramer et al. |
| 5,454,791 A | 10/1995 | Tovey et al. |
| 5,462,062 A | 10/1995 | Rubinstein et al. |
| 5,476,102 A | 12/1995 | Como et al. |
| 5,480,388 A | 1/1996 | Zadini et al. |
| 5,484,442 A | 1/1996 | Melker et al. |
| 5,497,787 A | 3/1996 | Nemesdy et al. |

(56) References Cited

U.S. PATENT DOCUMENTS

| | | | |
|---|---|---|---|
| 5,499,997 A | 3/1996 | Sharpe et al. | |
| 5,505,710 A | 4/1996 | Dorsey, III | |
| 5,505,737 A | 4/1996 | Gosselin et al. | |
| D369,858 S | 5/1996 | Baker et al. | |
| 5,514,097 A | 5/1996 | Knauer | |
| 5,526,820 A | 6/1996 | Khoury | |
| 5,526,821 A | 6/1996 | Jamshidi | |
| 5,526,822 A | 6/1996 | Burbank et al. | |
| 5,527,290 A | 6/1996 | Zadini et al. | |
| 5,529,580 A | 6/1996 | Kusunoki et al. | |
| 5,533,843 A | 7/1996 | Chung | |
| 5,549,565 A | 8/1996 | Ryan et al. | |
| 5,554,154 A | 9/1996 | Rosenberg | |
| 5,556,399 A | 9/1996 | Huebner | |
| 5,558,737 A | 9/1996 | Brown et al. | |
| 5,571,133 A | 11/1996 | Yoon | |
| 5,586,847 A | 12/1996 | Mattern, Jr. et al. | |
| 5,591,119 A | 1/1997 | Adair | |
| 5,591,188 A | 1/1997 | Waisman | |
| 5,595,186 A | 1/1997 | Rubinstein et al. | |
| 5,599,347 A | 2/1997 | Hart et al. | |
| 5,599,348 A | 2/1997 | Gentelia et al. | |
| 5,601,559 A | 2/1997 | Melker et al. | |
| 5,624,214 A | 4/1997 | Carroll | |
| 5,632,747 A | 5/1997 | Scarborough et al. | |
| 5,649,547 A | 7/1997 | Ritchart et al. | |
| 5,651,419 A | 7/1997 | Holzer et al. | |
| 5,672,155 A | 9/1997 | Riley et al. | |
| 5,685,820 A | 11/1997 | Riek et al. | |
| 5,687,802 A | 11/1997 | Spooner et al. | |
| 5,693,031 A | 12/1997 | Ryan et al. | |
| 5,709,275 A | 1/1998 | Anton | |
| 5,712,543 A | 1/1998 | Sjostrom | |
| 5,713,149 A | 2/1998 | Cady et al. | |
| 5,713,368 A | 2/1998 | Leigh | |
| 5,724,873 A | 3/1998 | Hillinger | |
| 5,728,124 A | 3/1998 | Cockburn et al. | |
| 5,733,262 A | 3/1998 | Paul | |
| 5,738,177 A * | 4/1998 | Schell | B25B 23/14 173/178 |
| 5,752,923 A | 5/1998 | Terwilliger | |
| 5,762,498 A | 6/1998 | Arnaldo | |
| 5,762,639 A | 6/1998 | Gibbs | |
| 5,766,221 A | 6/1998 | Benderev et al. | |
| 5,769,086 A | 6/1998 | Ritchart et al. | |
| 5,779,708 A | 7/1998 | Wu | |
| 5,800,389 A | 9/1998 | Burney et al. | |
| 5,801,454 A | 9/1998 | Leininger | |
| 5,807,275 A | 9/1998 | Jamshidi | |
| 5,807,277 A | 9/1998 | Swaim | |
| 5,809,653 A | 9/1998 | Everts et al. | |
| 5,810,826 A | 9/1998 | .ANG.kerfeldt et al. | |
| 5,817,052 A | 10/1998 | Johnson et al. | |
| 5,823,970 A | 10/1998 | Terwilliger | |
| D403,405 S | 12/1998 | Terwilliger | |
| D404,458 S | 1/1999 | Pruitt | |
| 5,858,005 A | 1/1999 | Kriesel | |
| 5,865,711 A | 2/1999 | Chen | |
| 5,868,711 A | 2/1999 | Kramer et al. | |
| 5,868,750 A | 2/1999 | Schultz | |
| 5,873,499 A | 2/1999 | Leschinsky et al. | |
| 5,873,510 A | 2/1999 | Hirai et al. | |
| 5,873,580 A | 2/1999 | Swenson et al. | |
| 5,885,226 A | 3/1999 | Rubinstein et al. | |
| 5,891,085 A | 4/1999 | Lilley et al. | |
| 5,893,851 A | 4/1999 | Umber et al. | |
| 5,906,797 A | 5/1999 | Orihara et al. | |
| 5,910,121 A | 6/1999 | Avaltroni et al. | |
| 5,911,701 A | 6/1999 | Miller et al. | |
| 5,911,708 A | 6/1999 | Feirstein | |
| 5,916,229 A | 6/1999 | Evans | |
| 5,919,172 A | 7/1999 | Golba, Jr. | |
| 5,921,562 A * | 7/1999 | Robison | B23B 31/28 279/128 |
| 5,921,987 A | 7/1999 | Stone | |
| 5,924,864 A | 7/1999 | Loge et al. | |
| 5,926,989 A | 7/1999 | Oliver, Sr. | |
| 5,927,976 A | 7/1999 | Wu | |
| 5,928,164 A | 7/1999 | Burbank et al. | |
| 5,928,238 A | 7/1999 | Scarborough et al. | |
| 5,928,241 A | 7/1999 | Menut et al. | |
| 5,938,636 A | 8/1999 | Kramer et al. | |
| 5,941,706 A | 8/1999 | Ura | |
| 5,941,841 A | 8/1999 | Mutch et al. | |
| 5,941,851 A | 8/1999 | Coffey et al. | |
| 5,945,896 A | 8/1999 | Miyamoto | |
| 5,947,989 A | 9/1999 | Shikhman et al. | |
| 5,951,026 A | 9/1999 | Harman, Jr. et al. | |
| 5,954,671 A | 9/1999 | O'Neill | |
| 5,954,701 A | 9/1999 | Matalon | |
| 5,960,575 A | 10/1999 | Chiovitt et al. | |
| 5,960,797 A | 10/1999 | Kramer et al. | |
| 5,980,469 A | 11/1999 | Burbank et al. | |
| 5,980,545 A | 11/1999 | Pacala et al. | |
| 5,984,020 A | 11/1999 | Meyer et al. | |
| 5,984,919 A | 11/1999 | Hilal et al. | |
| 5,989,257 A | 11/1999 | Tidwell et al. | |
| 5,993,417 A | 11/1999 | Yerfino et al. | |
| 5,993,454 A | 11/1999 | Longo | |
| 6,007,481 A | 12/1999 | Riek et al. | |
| 6,007,496 A | 12/1999 | Brannon | |
| 6,015,391 A | 1/2000 | Rishton et al. | |
| 6,017,348 A | 1/2000 | Hart et al. | |
| 6,018,094 A | 1/2000 | Fox | |
| 6,018,230 A | 1/2000 | Casey | |
| 6,022,324 A | 2/2000 | Skinner | |
| 6,025,683 A | 2/2000 | Philipp | |
| 6,027,458 A | 2/2000 | Janssens | |
| 6,033,369 A | 3/2000 | Goldenberg | |
| 6,033,408 A | 3/2000 | Gage et al. | |
| 6,033,411 A | 3/2000 | Preissman | |
| 6,042,585 A | 3/2000 | Norman | |
| 6,049,725 A | 4/2000 | Emmert et al. | |
| 6,050,754 A | 4/2000 | Thomas | |
| 6,050,955 A | 4/2000 | Bryan et al. | |
| 6,053,923 A | 4/2000 | Veca et al. | |
| 6,059,806 A | 5/2000 | Hoegerle | |
| 6,063,037 A | 5/2000 | Mittermeier et al. | |
| 6,066,938 A | 5/2000 | Hyodo et al. | |
| 6,071,284 A | 6/2000 | Fox | |
| 6,080,115 A | 6/2000 | Rubinstein | |
| 6,083,176 A | 7/2000 | Terwilliger | |
| 6,086,543 A | 7/2000 | Anderson et al. | |
| 6,086,544 A | 7/2000 | Hibner et al. | |
| 6,092,355 A | 7/2000 | Ishmael | |
| 6,096,042 A | 8/2000 | Herbert | |
| 6,098,042 A | 8/2000 | Huynh | |
| 6,102,887 A | 8/2000 | Altman | |
| 6,102,915 A | 8/2000 | Bresler et al. | |
| 6,106,484 A | 8/2000 | Terwilliger | |
| 6,110,128 A | 8/2000 | Andelin et al. | |
| 6,110,129 A | 8/2000 | Terwilliger | |
| 6,110,174 A | 8/2000 | Nichter | |
| 6,120,462 A | 9/2000 | Hibner et al. | |
| 6,126,670 A | 10/2000 | Walker et al. | |
| 6,129,106 A | 10/2000 | Kornelson et al. | |
| 6,135,769 A * | 10/2000 | Kwan | A61C 3/02 433/165 |
| 6,152,918 A | 11/2000 | Padilla et al. | |
| 6,154,995 A | 12/2000 | Lenoir et al. | |
| 6,159,163 A | 12/2000 | Strauss et al. | |
| 6,162,203 A | 12/2000 | Haaga | |
| 6,171,276 B1 | 1/2001 | Lippe et al. | |
| 6,183,442 B1 | 2/2001 | Athanasiou et al. | |
| 6,187,768 B1 | 2/2001 | Welle et al. | |
| 6,210,376 B1 | 4/2001 | Grayson | |
| 6,217,561 B1 | 4/2001 | Gibbs | |
| 6,221,029 B1 | 4/2001 | Mathis et al. | |
| 6,228,049 B1 | 5/2001 | Schroeder et al. | |
| 6,228,088 B1 | 5/2001 | Miller et al. | |
| 6,231,996 B1 | 5/2001 | Umeno et al. | |
| 6,238,355 B1 | 5/2001 | Daum | |
| 6,241,734 B1 | 6/2001 | Scribner et al. | |
| 6,242,009 B1 | 6/2001 | Batarseh et al. | |

(56) References Cited

U.S. PATENT DOCUMENTS

| | | |
|---|---|---|
| 6,247,110 B1 | 6/2001 | Huppenthal et al. |
| 6,247,928 B1 | 6/2001 | Meller et al. |
| 6,248,110 B1 | 6/2001 | Reiley et al. |
| 6,257,351 B1 | 7/2001 | Ark et al. |
| 6,261,272 B1 | 7/2001 | Gross et al. |
| 6,267,763 B1 | 7/2001 | Castro |
| 6,270,087 B1 | 8/2001 | Mickel et al. |
| 6,272,007 B1 | 8/2001 | Kitlas et al. |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,409 B1 | 10/2001 | Gutsche |
| 6,302,852 B1 | 10/2001 | Fleming, III et al. |
| 6,308,540 B1 | 10/2001 | Lee |
| 6,309,258 B1 | 10/2001 | Measley |
| 6,309,358 B1 | 10/2001 | Okubo |
| 6,312,394 B1 | 11/2001 | Fleming, III |
| 6,315,737 B1 | 11/2001 | Skinner |
| 6,321,855 B1* | 11/2001 | Barnes .................. B25B 13/06 173/132 |
| 6,325,806 B1 | 12/2001 | Fox |
| 6,328,701 B1 | 12/2001 | Terwilliger |
| 6,328,744 B1 | 12/2001 | Harari et al. |
| 6,349,496 B1 | 2/2002 | Neely |
| 6,358,252 B1 | 3/2002 | Shapira |
| 6,382,212 B1 | 5/2002 | Borchard |
| 6,402,701 B1 | 6/2002 | Kaplan et al. |
| 6,416,484 B1 | 7/2002 | Miller et al. |
| 6,419,490 B1 | 7/2002 | Weathers, Jr. |
| 6,425,388 B1 | 7/2002 | Korinchock |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,446,734 B1* | 9/2002 | Williams ................ B25F 5/02 173/1 |
| 6,450,973 B1 | 9/2002 | Murphy |
| 6,451,023 B1 | 9/2002 | Salazar et al. |
| 6,458,117 B1 | 10/2002 | Pollins, Sr. |
| 6,461,296 B1 | 10/2002 | Desai |
| 6,468,248 B2 | 10/2002 | Gibbs |
| 6,478,751 B1 | 11/2002 | Krueger et al. |
| 6,488,636 B2 | 12/2002 | Bryan et al. |
| 6,494,590 B1 | 12/2002 | Paganini et al. |
| 6,520,971 B1 | 2/2003 | Perry et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,537,242 B1 | 3/2003 | Palmer |
| 6,540,694 B1 | 4/2003 | Van Bladel et al. |
| 6,540,697 B2 | 4/2003 | Chen |
| 6,547,451 B1 | 4/2003 | Nishikawa et al. |
| 6,547,511 B1 | 4/2003 | Adams |
| 6,547,561 B2 | 4/2003 | Meller et al. |
| 6,547,755 B1 | 4/2003 | Lippe et al. |
| 6,549,511 B1 | 4/2003 | Prikryl |
| 6,550,786 B2 | 4/2003 | Gifford et al. |
| 6,554,779 B2 | 4/2003 | Viola et al. |
| 6,555,212 B2 | 4/2003 | Boiocchi et al. |
| 6,572,563 B2 | 6/2003 | Ouchi |
| 6,575,745 B2 | 6/2003 | Meller et al. |
| 6,575,919 B1 | 6/2003 | Reiley et al. |
| 6,582,399 B1 | 6/2003 | Smith et al. |
| 6,585,622 B1 | 7/2003 | Shum et al. |
| 6,595,362 B2 | 7/2003 | Penney et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stephens et al. |
| 6,622,731 B2 | 9/2003 | Daniel et al. |
| 6,626,173 B2 | 9/2003 | Genova et al. |
| 6,626,848 B2 | 9/2003 | Neuenfeldt |
| 6,626,887 B1 | 9/2003 | Wu |
| 6,638,235 B2 | 10/2003 | Miller et al. |
| 6,641,395 B2 | 11/2003 | Kumar et al. |
| 6,656,133 B2 | 12/2003 | Voegele et al. |
| 6,689,072 B2 | 2/2004 | Kaplan et al. |
| 6,690,308 B2 | 2/2004 | Hayami |
| 6,695,786 B2 | 2/2004 | Wang et al. |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,718,196 B1 | 4/2004 | Mah et al. |
| 6,726,649 B2 | 4/2004 | Swenson et al. |
| 6,730,043 B2 | 5/2004 | Krueger et al. |
| 6,730,044 B2 | 5/2004 | Stephens et al. |
| 6,733,458 B1 | 5/2004 | Steins et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,770,070 B1 | 8/2004 | Balbierz |
| 6,783,532 B2 | 8/2004 | Steiner et al. |
| 6,796,957 B2 | 9/2004 | Carpenter et al. |
| 6,839,789 B2 | 1/2005 | Kraemer et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,871,759 B2 | 3/2005 | Rake et al. |
| 6,872,187 B1 | 3/2005 | Stark et al. |
| 6,875,163 B2 | 4/2005 | Cercone et al. |
| 6,875,179 B2 | 4/2005 | Ferguson et al. |
| 6,875,183 B2 | 4/2005 | Cervi |
| 6,875,219 B2 | 4/2005 | Arramon et al. |
| 6,884,245 B2 | 4/2005 | Spranza, III |
| 6,887,209 B2 | 5/2005 | Kadziauskas et al. |
| 6,890,308 B2 | 5/2005 | Islam |
| 6,896,141 B2 | 5/2005 | McMichael et al. |
| 6,902,559 B2 | 6/2005 | Taufig |
| 6,905,466 B2 | 6/2005 | Salgo et al. |
| 6,905,486 B2 | 6/2005 | Gibbs |
| 6,916,292 B2 | 7/2005 | Morawski et al. |
| 6,930,461 B2 | 8/2005 | Rutkowski |
| 6,942,669 B2 | 9/2005 | Kurc |
| 6,947,669 B2 | 9/2005 | Wu et al. |
| 6,969,373 B2 | 11/2005 | Schwartz et al. |
| 7,001,342 B2 | 2/2006 | Faciszewski |
| 7,008,381 B2 | 3/2006 | Janssens |
| 7,008,383 B1 | 3/2006 | Damadian et al. |
| 7,008,394 B2 | 3/2006 | Geise et al. |
| 7,014,614 B2 | 3/2006 | Casula |
| 7,018,343 B2 | 3/2006 | Plishka |
| 7,025,732 B2 | 4/2006 | Thompson et al. |
| 7,033,324 B2 | 4/2006 | Giusti et al. |
| 7,063,672 B2 | 6/2006 | Schramm |
| 7,063,703 B2 | 6/2006 | Reo |
| 7,081,123 B2 | 7/2006 | Merboth et al. |
| 7,108,696 B2 | 9/2006 | Daniel et al. |
| 7,134,815 B2 | 11/2006 | Steer |
| 7,137,985 B2 | 11/2006 | Jahng |
| 7,169,127 B2 | 1/2007 | Epstein et al. |
| 7,182,752 B2 | 2/2007 | Stubbs et al. |
| 7,186,257 B2 | 3/2007 | Kim |
| 7,201,722 B2 | 4/2007 | Krueger |
| 7,207,949 B2 | 4/2007 | Miles et al. |
| 7,212,011 B2 | 5/2007 | Shimizu et al. |
| 7,226,450 B2 | 6/2007 | Athanasiou et al. |
| 7,229,401 B2 | 6/2007 | Kindlein |
| 7,278,972 B2 | 10/2007 | Lamoureux et al. |
| 7,285,112 B2 | 10/2007 | Stubbs et al. |
| 7,331,462 B2 | 2/2008 | Steppe |
| 7,331,930 B2 | 2/2008 | Faciszewski |
| 7,338,473 B2 | 3/2008 | Campbell et al. |
| 7,413,559 B2 | 8/2008 | Stubbs et al. |
| 7,513,722 B2 | 4/2009 | Greenberg et al. |
| 7,565,935 B1* | 7/2009 | Phillips .................. B23G 1/18 173/176 |

(56) References Cited

U.S. PATENT DOCUMENTS

| | | |
|---|---|---|
| 7,615,043 B2 | 11/2009 | Zhou |
| 7,670,328 B2 | 3/2010 | Miller |
| 7,699,850 B2 | 4/2010 | Miller |
| 7,736,322 B2 | 6/2010 | Roe et al. |
| 7,798,331 B2 | 9/2010 | Hardin et al. |
| 7,811,260 B2 | 10/2010 | Miller et al. |
| 7,815,642 B2 | 10/2010 | Miller |
| 7,850,620 B2 | 12/2010 | Miller et al. |
| 7,854,724 B2 | 12/2010 | Stearns et al. |
| 7,899,528 B2 | 3/2011 | Miller et al. |
| 7,934,333 B1 | 5/2011 | Tuz |
| 7,951,089 B2 | 5/2011 | Miller |
| 7,988,643 B2 | 8/2011 | Hoffmann et al. |
| 8,038,664 B2 | 10/2011 | Miller et al. |
| 8,088,189 B2 | 1/2012 | Matula et al. |
| 8,092,457 B2 | 1/2012 | Oettinger et al. |
| 8,142,365 B2 | 3/2012 | Miller |
| 8,216,189 B2 | 7/2012 | Stubbs et al. |
| 8,217,561 B2 | 7/2012 | Fukuzawa et al. |
| 8,277,411 B2 | 10/2012 | Gellman |
| 8,282,565 B2 | 10/2012 | Mahapatra et al. |
| 8,308,693 B2 | 11/2012 | Miller et al. |
| 8,317,815 B2 | 11/2012 | Mastri et al. |
| 8,419,683 B2 | 4/2013 | Miller et al. |
| 8,480,632 B2 | 7/2013 | Miller et al. |
| 8,506,568 B2 | 8/2013 | Miller |
| 8,641,715 B2 | 2/2014 | Miller |
| 8,656,929 B2 | 2/2014 | Miller et al. |
| 8,668,698 B2 | 3/2014 | Miller et al. |
| 8,684,978 B2 | 4/2014 | Miller et al. |
| 8,690,791 B2 | 4/2014 | Miller |
| 8,715,219 B2 | 5/2014 | Stearns et al. |
| 8,715,287 B2 | 5/2014 | Miller |
| 8,720,097 B2 | 5/2014 | Derman |
| 8,812,101 B2 | 8/2014 | Miller et al. |
| 8,814,807 B2 | 8/2014 | Hulvershorn et al. |
| 8,870,872 B2 | 10/2014 | Miller |
| 8,876,826 B2 | 11/2014 | Miller |
| 8,920,388 B2 | 12/2014 | Slocum et al. |
| 8,926,525 B2 | 1/2015 | Hulvershorn et al. |
| 8,944,069 B2 | 2/2015 | Miller et al. |
| 8,961,451 B2 | 2/2015 | Stearns et al. |
| 8,974,410 B2 | 3/2015 | Miller et al. |
| 8,974,569 B2 | 3/2015 | Matula et al. |
| 8,992,535 B2 | 3/2015 | Miller |
| 8,998,348 B2 | 4/2015 | Frank |
| 8,998,848 B2 | 4/2015 | Miller et al. |
| 9,067,030 B2 | 6/2015 | Stearns et al. |
| 9,072,543 B2 | 7/2015 | Miller et al. |
| 9,078,637 B2 | 7/2015 | Miller |
| 9,095,372 B2 | 8/2015 | Stearns et al. |
| 9,110,104 B2 | 8/2015 | Chung et al. |
| 9,186,172 B2 | 11/2015 | Velez Rivera |
| 9,199,047 B2 | 12/2015 | Stearns et al. |
| 9,295,487 B2 | 3/2016 | Miller et al. |
| 9,314,228 B2 | 4/2016 | Miller |
| 9,314,270 B2 | 4/2016 | Miller |
| 9,393,364 B2 | 7/2016 | Fischer, Jr. |
| 9,439,667 B2 | 9/2016 | Miller |
| 9,451,968 B2 | 9/2016 | Miller et al. |
| 9,504,477 B2 | 11/2016 | Miller et al. |
| 9,545,243 B2 | 1/2017 | Miller et al. |
| 9,662,160 B2 | 5/2017 | Beale et al. |
| 9,717,564 B2 | 8/2017 | Miller et al. |
| 9,717,847 B2 | 8/2017 | Miller et al. |
| 9,826,984 B2 | 11/2017 | McGinley et al. |
| 9,872,703 B2 | 1/2018 | Miller et al. |
| 10,016,217 B2 | 7/2018 | Miller |
| 10,052,111 B2 | 8/2018 | Miller et al. |
| 10,081,414 B2 | 9/2018 | Le Devehat et al. |
| 10,149,686 B2 | 12/2018 | Anderson |
| 10,245,010 B2 | 4/2019 | Miller et al. |
| 10,258,783 B2 | 4/2019 | Miller et al. |
| 10,456,149 B2 | 10/2019 | Miller |
| 10,512,474 B2 | 12/2019 | Miller et al. |
| 10,722,247 B2 | 7/2020 | Browne et al. |
| 10,806,491 B2 | 10/2020 | Miller et al. |
| 10,893,875 B2 | 1/2021 | Miller |
| 11,103,281 B2 | 8/2021 | Miller |
| 11,103,282 B1 | 8/2021 | Miller et al. |
| 2001/0005778 A1 | 6/2001 | Ouchi |
| 2001/0014439 A1* | 8/2001 | Meller ............... A61C 1/081 433/50 |
| 2001/0026051 A1 | 10/2001 | Gifford et al. |
| 2001/0034527 A1 | 10/2001 | Scribner et al. |
| 2001/0047183 A1 | 11/2001 | Privitera et al. |
| 2001/0053888 A1 | 12/2001 | Athanasiou et al. |
| 2002/0022788 A1 | 2/2002 | Corvi et al. |
| 2002/0029007 A1 | 3/2002 | Bryan et al. |
| 2002/0042581 A1 | 4/2002 | Cervi |
| 2002/0050364 A1 | 5/2002 | Suzuki et al. |
| 2002/0055713 A1 | 5/2002 | Gibbs |
| 2002/0082519 A1 | 6/2002 | Miller et al. |
| 2002/0091039 A1 | 7/2002 | Reinbold et al. |
| 2002/0096343 A1 | 7/2002 | Potter et al. |
| 2002/0120197 A1 | 8/2002 | Kleffner et al. |
| 2002/0120212 A1 | 8/2002 | Ritchart et al. |
| 2002/0133148 A1 | 9/2002 | Daniel et al. |
| 2002/0138021 A1 | 9/2002 | Pflueger |
| 2002/0143269 A1 | 10/2002 | Neuenfeldt |
| 2002/0151821 A1 | 10/2002 | Castellacci |
| 2002/0151902 A1 | 10/2002 | Riedel et al. |
| 2002/0158102 A1* | 10/2002 | Patton ............... F04B 35/04 227/8 |
| 2002/0177822 A1 | 11/2002 | St. Cyr et al. |
| 2003/0009132 A1 | 1/2003 | Schwartz et al. |
| 2003/0023256 A1 | 1/2003 | Estes et al. |
| 2003/0028146 A1 | 2/2003 | Aves |
| 2003/0032939 A1 | 2/2003 | Gibbs |
| 2003/0036747 A1 | 2/2003 | Ie et al. |
| 2003/0050574 A1 | 3/2003 | Krueger |
| 2003/0078586 A1 | 4/2003 | Shapira |
| 2003/0078589 A1 | 4/2003 | Preissman |
| 2003/0114858 A1 | 6/2003 | Athanasiou et al. |
| 2003/0125639 A1 | 7/2003 | Fisher et al. |
| 2003/0144104 A1 | 7/2003 | Ryberg |
| 2003/0149436 A1 | 8/2003 | Mcdowell et al. |
| 2003/0153842 A1 | 8/2003 | Lamoureux et al. |
| 2003/0173178 A1* | 9/2003 | Sasaki ............... F16D 41/206 192/3.51 |
| 2003/0191414 A1 | 10/2003 | Reiley et al. |
| 2003/0195436 A1 | 10/2003 | Van Bladel et al. |
| 2003/0195524 A1 | 10/2003 | Barner |
| 2003/0199787 A1 | 10/2003 | Schwindt |
| 2003/0199879 A1 | 10/2003 | Spranza |
| 2003/0205987 A1 | 11/2003 | Barlev et al. |
| 2003/0212343 A1 | 11/2003 | Plishka |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2003/0233114 A1 | 12/2003 | Merboth et al. |
| 2004/0010236 A1 | 1/2004 | Morawski et al. |
| 2004/0019297 A1 | 1/2004 | Angel |
| 2004/0019299 A1 | 1/2004 | Ritchart et al. |
| 2004/0031721 A1 | 2/2004 | Mann |
| 2004/0032179 A1 | 2/2004 | Du |
| 2004/0034280 A1 | 2/2004 | Privitera et al. |
| 2004/0049128 A1 | 3/2004 | Miller et al. |
| 2004/0049157 A1 | 3/2004 | Plishka et al. |
| 2004/0049205 A1 | 3/2004 | Lee et al. |
| 2004/0064136 A1 | 4/2004 | Papineau et al. |
| 2004/0073139 A1 | 4/2004 | Hirsch et al. |
| 2004/0092946 A1 | 5/2004 | Bagga et al. |
| 2004/0127814 A1 | 7/2004 | Negroni |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0167428 A1 | 8/2004 | Quick et al. |
| 2004/0191897 A1 | 9/2004 | Muschler |
| 2004/0210161 A1 | 10/2004 | Burdorff et al. |
| 2004/0210196 A1 | 10/2004 | Bush et al. |
| 2004/0210198 A1 | 10/2004 | Shih |

(56) References Cited

U.S. PATENT DOCUMENTS

| | | |
|---|---|---|
| 2004/0215102 A1 | 10/2004 | Ikehara et al. |
| 2004/0220497 A1 | 11/2004 | Findlay et al. |
| 2004/0249306 A1 | 12/2004 | Islam |
| 2004/0249389 A1 | 12/2004 | Kim |
| 2004/0259254 A1 | 12/2004 | Honmou et al. |
| 2005/0027210 A1 | 2/2005 | Miller |
| 2005/0033275 A1 | 2/2005 | Hoegerle et al. |
| 2005/0033304 A1 | 2/2005 | O'Heeron |
| 2005/0040060 A1 | 2/2005 | Andersen et al. |
| 2005/0043714 A1 | 2/2005 | Zhou |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller et al. |
| 2005/0116673 A1 | 6/2005 | Carl et al. |
| 2005/0119660 A1 | 6/2005 | Bourlion et al. |
| 2005/0124915 A1 | 6/2005 | Eggers et al. |
| 2005/0131345 A1 | 6/2005 | Miller |
| 2005/0148940 A1 | 7/2005 | Miller |
| 2005/0159677 A1 | 7/2005 | Shabaz et al. |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0236940 A1 | 10/2005 | Rockoff |
| 2005/0261693 A1 | 11/2005 | Miller et al. |
| 2006/0011506 A1 | 1/2006 | Riley |
| 2006/0015066 A1 | 1/2006 | Turieo et al. |
| 2006/0036212 A1 | 2/2006 | Miller |
| 2006/0043685 A1* | 3/2006 | Kozak ............. B25B 23/0035 279/137 |
| 2006/0052790 A1 | 3/2006 | Miller |
| 2006/0074345 A1 | 4/2006 | Hibner |
| 2006/0074425 A1 | 4/2006 | Sutterlin et al. |
| 2006/0079774 A1 | 4/2006 | Anderson |
| 2006/0089565 A1 | 4/2006 | Schramm |
| 2006/0111724 A1 | 5/2006 | Yeung Wai Ping |
| 2006/0115066 A1 | 6/2006 | Levien et al. |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0151188 A1 | 7/2006 | Bodine et al. |
| 2006/0167377 A1 | 7/2006 | Ritchart et al. |
| 2006/0167378 A1 | 7/2006 | Miller |
| 2006/0167379 A1 | 7/2006 | Miller |
| 2006/0173480 A1 | 8/2006 | Zhang |
| 2006/0184063 A1 | 8/2006 | Miller |
| 2006/0189940 A1 | 8/2006 | Kirsch |
| 2006/0192350 A1 | 8/2006 | Kleine et al. |
| 2006/0206132 A1 | 9/2006 | Conquergood et al. |
| 2006/0237205 A1* | 10/2006 | Sia ................. B25B 23/1405 173/48 |
| 2007/0016100 A1 | 1/2007 | Miller |
| 2007/0024013 A1 | 2/2007 | Hauptmann et al. |
| 2007/0049945 A1 | 3/2007 | Miller |
| 2007/0084742 A1 | 4/2007 | Miller et al. |
| 2007/0120331 A1 | 5/2007 | Manschitz et al. |
| 2007/0149920 A1 | 6/2007 | Michels et al. |
| 2007/0209957 A1 | 9/2007 | Glenn et al. |
| 2007/0213735 A1 | 9/2007 | Saadat et al. |
| 2007/0256914 A1 | 11/2007 | Lohr et al. |
| 2007/0270712 A1 | 11/2007 | Wiksell et al. |
| 2007/0270775 A1 | 11/2007 | Miller et al. |
| 2008/0015467 A1 | 1/2008 | Miller |
| 2008/0015468 A1 | 1/2008 | Miller |
| 2008/0015623 A1 | 1/2008 | Deck |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0072719 A1 | 3/2008 | Kozak |
| 2008/0086160 A1 | 4/2008 | Mastri et al. |
| 2008/0087448 A1 | 4/2008 | Happ |
| 2008/0140014 A1 | 6/2008 | Miller et al. |
| 2008/0177200 A1 | 7/2008 | Ikehara et al. |
| 2008/0215056 A1 | 9/2008 | Miller et al. |
| 2008/0221580 A1 | 9/2008 | Miller et al. |
| 2008/0243163 A1 | 10/2008 | Masseglia et al. |
| 2008/0262383 A1 | 10/2008 | Routhier et al. |
| 2008/0302551 A1* | 12/2008 | Komuro ............. B25F 5/008 173/217 |
| 2009/0069716 A1 | 3/2009 | Freeman et al. |
| 2009/0093677 A1 | 4/2009 | Smith |
| 2009/0131832 A1 | 5/2009 | Sacristan et al. |
| 2009/0194446 A1 | 8/2009 | Miller et al. |
| 2009/0248029 A1 | 10/2009 | Paulos |
| 2009/0311061 A1* | 12/2009 | Santamarina ....... B25B 23/0035 408/239 A |
| 2010/0137740 A1 | 6/2010 | Miller |
| 2010/0204611 A1 | 8/2010 | Zambelli |
| 2010/0298784 A1 | 11/2010 | Miller |
| 2011/0046477 A1 | 2/2011 | Hulvershorn et al. |
| 2011/0046507 A1 | 2/2011 | Herndon |
| 2011/0071572 A1 | 3/2011 | Sixto et al. |
| 2011/0082387 A1 | 4/2011 | Miller et al. |
| 2011/0098604 A1 | 4/2011 | Miller |
| 2011/0125084 A1 | 5/2011 | Stearns et al. |
| 2011/0184425 A1 | 7/2011 | Cheraux |
| 2011/0186456 A1 | 8/2011 | Bertazzoni et al. |
| 2011/0203821 A1 | 8/2011 | Puzio et al. |
| 2011/0251518 A1 | 10/2011 | Swisher et al. |
| 2011/0288405 A1 | 11/2011 | Razavi et al. |
| 2011/0306841 A1 | 12/2011 | Lozman et al. |
| 2012/0109061 A1 | 5/2012 | Miller et al. |
| 2012/0150101 A1 | 6/2012 | Stearns et al. |
| 2012/0165832 A1 | 6/2012 | Oostman et al. |
| 2012/0283582 A1 | 11/2012 | Mahapatra et al. |
| 2012/0323071 A1 | 12/2012 | Gellman |
| 2012/0330184 A1 | 12/2012 | Mahapatra et al. |
| 2013/0213843 A1 | 8/2013 | Knight et al. |
| 2014/0005657 A1 | 1/2014 | Brannan et al. |
| 2014/0188038 A1 | 7/2014 | Stearns et al. |
| 2014/0231302 A1 | 8/2014 | Goyal |
| 2014/0262408 A1 | 9/2014 | Woodard |
| 2014/0311302 A1 | 10/2014 | Taguchi et al. |
| 2014/0336567 A1 | 11/2014 | Stearns et al. |
| 2014/0343454 A1 | 11/2014 | Miller et al. |
| 2014/0358070 A1 | 12/2014 | Stearns et al. |
| 2015/0025363 A1 | 1/2015 | Hulvershorn et al. |
| 2015/0057530 A1 | 2/2015 | Roggeveen et al. |
| 2015/0112261 A1 | 4/2015 | Bassett et al. |
| 2015/0127006 A1 | 5/2015 | Miller |
| 2015/0129456 A1 | 5/2015 | Miller et al. |
| 2015/0173818 A1 | 6/2015 | Baroud et al. |
| 2015/0202390 A1 | 7/2015 | Stearns et al. |
| 2015/0202391 A1 | 7/2015 | Stearns et al. |
| 2015/0223786 A1 | 8/2015 | Morgan et al. |
| 2015/0230823 A1 | 8/2015 | Morgan et al. |
| 2015/0342635 A1 | 12/2015 | Tsamir et al. |
| 2015/0366569 A1 | 12/2015 | Miller |
| 2016/0081732 A1 | 3/2016 | Baroud |
| 2017/0036328 A1 | 2/2017 | Chen |
| 2017/0266790 A1 | 9/2017 | Chuang |
| 2018/0056095 A1 | 3/2018 | Messerly et al. |
| 2020/0054350 A1 | 2/2020 | Miller |
| 2020/0214722 A1 | 7/2020 | Miller |
| 2021/0045753 A1 | 2/2021 | Miller et al. |
| 2021/0052286 A1 | 2/2021 | Miller et al. |

FOREIGN PATENT DOCUMENTS

| | | |
|---|---|---|
| CA | 2454600 A1 | 2/2003 |
| CN | 2294028 Y | 10/1998 |
| CN | 2320209 Y | 5/1999 |
| CN | 2664675 Y | 12/2004 |
| DE | 10057831 A1 | 5/2002 |
| DE | 10057931 A1 | 8/2002 |

(56) References Cited

FOREIGN PATENT DOCUMENTS

| | | |
|---|---|---|
| EP | 0271775 A2 | 6/1988 |
| EP | 0517000 A2 | 12/1992 |
| EP | 0528478 A1 | 2/1993 |
| EP | 0807412 A1 | 11/1997 |
| EP | 0853349 A1 | 7/1998 |
| EP | 1099450 A1 | 5/2001 |
| EP | 1314452 A1 | 5/2003 |
| EP | 1421907 A1 | 5/2004 |
| EP | 1447050 A2 | 8/2004 |
| EP | 2068725 A2 | 6/2009 |
| EP | 2177171 A1 | 4/2010 |
| EP | 3153116 A1 | 4/2017 |
| FR | 853349 A | 3/1940 |
| FR | 2457105 A1 | 12/1980 |
| FR | 2516386 A1 | 5/1983 |
| FR | 2931451 A1 | 11/2009 |
| GB | 0322382 A | 12/1929 |
| GB | 0629824 | 9/1949 |
| GB | 2099703 A | 12/1982 |
| GB | 2130890 A | 6/1984 |
| JP | 59-119808 A | 7/1984 |
| JP | 61-032633 Y2 | 9/1986 |
| JP | 61-032663 Y2 | 9/1986 |
| JP | 64-052433 A | 2/1989 |
| JP | 1052433 A | 2/1989 |
| JP | 06-132663 A | 5/1994 |
| JP | 10-052433 A | 2/1998 |
| JP | 2001505076 A | 4/2001 |
| JP | 6132663 B2 | 5/2017 |
| WO | 9208410 A1 | 5/1992 |
| WO | 9307819 A2 | 4/1993 |
| WO | 93/25151 A1 | 12/1993 |
| WO | 94/07553 A1 | 4/1994 |
| WO | 9631164 A1 | 10/1996 |
| WO | 9806337 A1 | 2/1998 |
| WO | 9852638 A2 | 11/1998 |
| WO | 9918866 A1 | 4/1999 |
| WO | 9952444 A1 | 10/1999 |
| WO | 0009024 A1 | 2/2000 |
| WO | 00/10465 A1 | 3/2000 |
| WO | 00/56220 A1 | 9/2000 |
| WO | 01/78590 A1 | 10/2001 |
| WO | 01/93931 A1 | 12/2001 |
| WO | 02/41791 A1 | 5/2002 |
| WO | 02/41792 A1 | 5/2002 |
| WO | 02/096497 A1 | 12/2002 |
| WO | 03/015637 A1 | 2/2003 |
| WO | 2003/101307 A1 | 12/2003 |
| WO | 2005072625 A2 | 8/2005 |
| WO | 2005110259 A1 | 11/2005 |
| WO | 2005112800 A2 | 12/2005 |
| WO | 2008/033871 A2 | 3/2008 |
| WO | 2008/033874 A2 | 3/2008 |
| WO | 2008081438 A1 | 7/2008 |
| WO | 2009/070896 A1 | 6/2009 |
| WO | 2011/070593 A1 | 6/2011 |
| WO | 2011/123703 A1 | 10/2011 |
| WO | 2012/175946 A1 | 12/2012 |

OTHER PUBLICATIONS

Chineese Office Action with English translation; Application No. 200910006631.3; pp. 12, dated Mar. 11, 2010.
Chinese Office Action w/english translation; Application No. 200680021872.X; pp. 8, dated Nov. 6, 2009.
Chinese Office Action with English translation, Application No. 2005800003261, 9 pgs, dated Jan. 16, 2009.
Chinese Office Action with English translation; Application No. 200380000022.0; pp. 10; dated Dec. 13, 2010.
Chinese Office Action with English translation; Application No. 200780000585.5; pp. 15, dated Nov. 19, 2010.
Chinese Office Action with English translation; Application No. 200780001190. 7; 12 pgs., dated Jun. 2, 2010.
Chinese Office Action with English translation; Application No. 200780001196; 12 pgs., dated Jul. 12, 2010.
Chinese Office Action with English translation; Application No. 200780001198.3; pp. 13, dated Apr. 27, 2010.
Chinese Office Action with English translation; Application No. 200830000022.0; pp. dated May 25, 2012.
Chinese Office Action with English translation; Application No. 200880000022.0; Pgs. dated Sep. 22, 2011.
Chinese Office Action with English translation; Application No. 200880000182.5; 12 pages, dated Sep. 10, 2010.
Chinese Office Action with English translation; Application No. 200910006631.3; p. 9, dated Nov. 11, 2010.
Chinese Office Action, Application No. 200780000590.6, (with English translation), (13 pages), dated Aug. 21, 2009.
Chinese Office Action, Application No. 200780001188.X, (with English translation), (8 pgs) dated Nov. 9, 2010.
Chinese Office Action, Notification of the Fourth Office Action, Application No. 200880000022.0, dated Jan. 7, 2013.
Chinese Office Action, Notification of the Second Office Action, Application No. 200780000590.6, dated Mar. 1, 2010.
Communication Pursuant to Article 94(3) EPC in European Application No. 05712091.7 dated Apr. 8, 2008.
Communication relating to the results of the partial International Search Report for dated PCT/US2005/002484, 6 pages dated May 19, 2005.
Edited by Frederick A. Matsen III M.D., Comparlmental Syndromes, About Compartmental Syndromes, Generic Trauma Content http://www.orthop.washington.edu/uw/ . . . , pp. 1-45.
European Extended Search Report, Application No. EP08021732.6, 7 pages, dated Nov. 13, 2009.
European Extended Search Report, Application No. EP10153350.3, 5 pages, dated Mar. 11, 2010.
European Office Action and Search Report, Application No. 09150973. 7, 8 pages, dated Oct. 23, 2009.
European Office Action dated Apr. 8, 2008 and Response dated May 15, 2008 , EP Application No. 05712091.7.
European Office Action dated Dec. 22, 2011 and Response dated Jun. 29, 2012 , EP Application No. 09150973.7.
European Office Action dated Feb. 21, 2007 and Response dated Jun. 27, 2007 , EP Application No. 05712091.7.
European Office Action dated Jan. 19, 2011 and Response dated Jul. 21, 2011 , EP Application No. 09150973.7.
European Office Action dated Sep. 21, 2007 and Response dated Nov. 26, 2007, EP Application No. 05712091.7.
European Office Action dated Sep. 8, 2010 and Response dated Mar. 17, 2011, EP Application No. 10153350.3.
European Office Action, Application No. 10 153 350.3, 5 pages, dated Sep. 8, 2010.
European Patent Office, Communication from Examining Division for European Patent Application No. 08799753.2, dated Apr. 10, 2014.
European Patent Office, Communication from Examining Division for European Patent Application No. 08799753.2, dated May 18, 2015.
European Patent Office, Communication from Examining Division for European Patent Application No. 08799753.2, dated Sep. 29, 2014.
European Patent Office, European Search Report for European Patent Application No. 08799753.2, dated May 23, 2013.
European Search Report for European Patent Application No. 07842288.8, dated Mar. 16, 2011.
European Search Report issued in European Patent Application No. 17198059.2 dated Jan. 29, 2018.
European Telephone Consultation Report dated Apr. 21, 2009 and Response dated Jun. 24, 2009 , EP Application No. 08158699 .2.
European Telephone Consultation Report dated Sep. 23, 2009 and Response dated Oct. 28, 2009 , EP Application No. 08158699 .2.
Extended European Search Report for European application 07842285. 4. dated Mar. 17, 2011.
Extended European Search Report for European application 07842286. 2. dated Mar. 18, 2011.
Extended European Search Report in Application No. EP 10153350.3 dated Mar. 11, 2010.

(56) References Cited

OTHER PUBLICATIONS

Final Office Action, U.S. Appl. No. 11/064,156, 12 pages, dated Jun. 19, 2009.
Final Office Action, U.S. Appl. No. 11/781,568, 19 pages, dated Jun. 17, 2009.
Final Office Action, U.S. Appl. No. 11/781,597, 14 pages, dated Nov. 17, 2009.
Final Office Action, U.S. Appl. No. 11/853,685, 21 pages, dated Jun. 24, 2009.
International PCT Search Report and Written Opinion PCT/US2005/002484, 15 pages, dated Jul. 22, 2005.
International PCT Search Report and Written Opinion PCT/US2004/037753, 16 pages, dated Jul. 8, 2005.
International PCT Search Report PCT/US03/17167, 8 pages, dated Sep. 16, 2003.
International PCT Search Report PCT/US03/17203, 8 pages, dated Sep. 16, 2003.
International PCT Search Report PCT/US2004/037753, 6 pages, dated Apr. 19, 2005.
Astrom, K.G., "Automatic Biopsy Instruments Used Through a Coaxial Bone Biopsy System with an Eccentric Drill Tip," Acta Radiological, 1995; 36:237-242 (May 1995).
Astrom, K. Gunnar O., "CT-guided Transsternal Core Biopsy of Anterior Mediastinal Masses," Radiology 1996; 199:564-567 (May 1996).
Liakat A. Parapia, "Trepanning or trephines: a history of bone marrow biopsy", British Journal of Haematology, pp. 14-19 (2007).
Vidacare Corporation Comments on Infusion Nurses Society Position Paper on Intraosseous Vascular Access, Vidacare, May 4, 2009, 6 pages.
Pediatric Emergency, Intraosseous Infusion for Administration of Fluids and Drugs, www.cookgroup.com, 1 pg. (2000).
Wichael Totty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages (2008).
Buckley et al., CT-guided bone biopsy: Initial experience with commercially available hand held Black and Decker drill, European Journal of Radiology, 61 pp. 176-180 (2007).
Hakan et al., CT-guided Bone Biopsy Performed by Means of Coaxial Biopsy System with an Eccentric Drill, Radiology, pp. 549-552 (Aug. 1993).
Gunal et al., Compartment Syndrome After Intraosseous Infusion: An Experimental Study in Dogs, Journal of Pediatric Surgery, vol. 31, No. 11, pp. 1491-1493 (Nov. 1996).
BioAccess.com, Single Use Small Bone Power Tool—How It Works, 1 page (Jun. 9, 2008).
Richard Cummins et al., "ACLS-Principles and Practice", ACLS— The Reference Textbook, American Heart Association, pp. 214-218 (2003).
Riley et al., "A Pathologist's Perspective on Bone Marrow Aspiration and Biopsy: I. Performing a Bone Marrow Examination", Journal of Clinical Laboratory Analysis, 18:70-90 (2004), 24 pages.
"Proven reliability for quality bone marrow samples", Special Procedures, Cardinal Health, 6 pages (2003).
F.A.S.T. 1 Intraosseous Infusion System with Depth-Control Mechanism Brochure, 6 pages (2000).
Pediatrics, "2005 American Heart Association Guidelines for Cardiopulmonary Resuscitation and Emergency Cardiovascular Care of Pediatric and Neonatal Patients: Pediatric Advanced Life Support," www.pediatrics.org, Official Journal of the American Academy of Pediatrics, 26 pages (Feb. 21, 2007).
Notice of Allowance in U.S. Appl. No. 12/331,979 dated Jul. 17, 2013.
Notice of Allowance in U.S. Appl. No. 12/331,979, dated Dec. 23, 2013.
Notice of Allowance in U.S. Appl. No. 12/899,696 dated Aug. 27, 2013.
Notice of Allowance in U.S. Appl. No. 12/899,696 dated Jul. 18, 2013.
Notice of Allowance in U.S. Appl. No. 14/271,144 dated Jul. 22, 2014.
Notice of Allowance in U.S. Appl. No. 12/259,745 dated Nov. 7, 2014.
Notice of Allowance in U.S. Appl. No. 12/407,651 dated Jun. 11, 2014.
Notice of Allowance in U.S. Appl. No. 12/427,310, dated Nov. 29, 2013.
Notice of Allowance in U.S. Appl. No. 12/718,638, dated Aug. 3, 2015.
Notice of Allowance in U.S. Appl. No. 12/899,696, dated Nov. 12, 2013.
Notice of Allowance in U.S. Appl. No. 13/966,104, dated Aug. 17, 2015.
Notice of Allowance issued in U.S. Appl. No. 11/042,912, dated Mar. 27, 2013.
Notice of Allowance issued in U.S. Appl. No. 11/253,467, dated Mar. 29, 2013.
Notice of Allowance issued in U.S. Appl. No. 11/253,467, dated Mar. 4, 2014.
Notice of Allowance issued in U.S. Appl. No. 11/253,959 dated May 20, 2013.
Notice of Allowance issued in U.S. Appl. No. 11/253,959, dated Mar. 14, 2013.
Notice of Allowance issued in U.S. Appl. No. 11/853,678, dated Mar. 27, 2013.
Notice of Allowance issued in U.S. Appl. No. 11/853,701, dated Mar. 14, 2013.
Notice of Allowance issued in U.S. Appl. No. 12/427,310, dated Jun. 5, 2013.
Notice of Allowance issued in U.S. Appl. No. 12/554,664 dated Jul. 20, 2012.
Notice of Allowance issued in U.S. Appl. No. 12/554,708 dated Jul. 11, 2012.
Notice of Allowance issued in U.S. Appl. No. 12/718,606, dated Mar. 6, 2013.
Notice of Allowance issued in U.S. Appl. No. 12/718,606, dated Oct. 11, 2012.
Notification of First Chinese Office Action, Application No. 201410112780.9, dated May 27, 2015.
Notification of the First Chinese Office Action, Application No. 200580003261.8, 3 pages, dated Mar. 21, 2008.
Office Action for for Chinese application 200380000182.5 (English translation) dated Jun. 27, 2013.
Office Action for Canadian application 2,612,483, dated Dec. 27, 2013.
Office Action for Chinese application 201210169456.0 with English translation, dated Aug. 28, 2013.
Office Action for Chinese application 201210169546.0 with English translation. dated Apr. 18, 2014.
Office Action for European application 03731475.4, dated Oct. 11, 2007.
Office Action for European application 05712091.7, dated Sep. 21, 2007.
Office Action for European application 07842284.7. dated May 3, 2012.
Office Action for European application 07842285.4. dated May 3, 2012.
Office Action for European application 07842286.2. dated Apr. 30, 2012.
Office Action for European application 07842288.8. dated May 3, 2012.
Office Action for European application 08021732.6. dated Oct. 2, 2013.
Office Action for European application 09155111.9-2310, dated Nov. 25, 2009.
Office Action for Japanese Application No. 2004-508670 with English Translation, dated Aug. 31, 2010.
Office Action for Taiwanese application 093134480 (English Translation), dated Feb. 11, 2011.
Office Action for U.S. Appl. No. 10/449,503, dated Apr. 1, 2009.

(56) References Cited

OTHER PUBLICATIONS

Office Action for U.S. Appl. No. 11/042,912, dated Mar. 19, 2010.
Office Action for U.S. Appl. No. 11/042,912, dated Nov. 28, 2008.
Office Action for U.S. Appl. No. 11/190,331, dated Mar. 23, 2009.
Office Action for U.S. Appl. No. 11/253,467, dated Apr. 28, 2011.
Office Action for U.S. Appl. No. 11/253,467, dated Jul. 22, 2010.
Office Action for U.S. Appl. No. 11/253,467, dated Oct. 29, 2010.
Office Action for U.S. Appl. No. 11/253,959, dated Aug. 5, 2010.
Office Action for U.S. Appl. No. 11/253,959, dated Mar. 30, 2011.
Office Action for U.S. Appl. No. 11/253,959, dated Oct. 18, 2010.
Office Action for U.S. Appl. No. 11/427,501, dated Aug. 7, 2008.
Office Action for U.S. Appl. No. 11/427,501, dated Oct. 21, 2009.
Office Action for U.S. Appl. No. 11/427,501. dated May 13, 2009.
Office Action for U.S. Appl. No. 12/905,659, dated Mar. 21, 2011.
Office Action for U.S. Appl. No. 12/905,659, dated May 13, 2011.
Office Action in Canadian Patent Application No. 2,612,433, dated Aug. 22, 2014.
Office Action in Canadian Patent Application No. 2,612,483, dated Aug. 22, 2014.
Office Action in European Application No. 03756317.8 dated Dec. 28, 2006.
Office Action in European Application No. 08158699.2 dated Nov. 4, 2008.
Office Action issued in Chinese Application No. 200910006631.3, dated Mar. 22, 2011.
Office Action issued in Chinese Patent Application No. 201010144512.7, dated Feb. 23, 2011.
Office Action issued in Chinese Patent Application No. 201010144520.1, dated Jan. 27, 2011.
Office Action issued in European Application No. 09155111.9 dated Nov. 25, 2009.
Office Communication for European application 09150973.7-1269, dated Jan. 19, 2011.
Office Communication for European Patent Application No. 07842288.8, dated Mar. 12, 2015.
Office Communication in European Application No. 08021732.6, dated Jun. 20, 2013.
Office Communication in European Application No. 10153350.3, dated Jun. 14, 2011.
Office Communication issued in Chinese Patent Application No. 200910138130.0, dated Oct. 10, 2011.
Office Communication issued in European Patent Application No. 09150973.7, dated Dec. 22, 2011.
Office Communication issued in Taiwanese Patent Application No. 093134480, dated Jan. 15, 2011.
PCT Invitation to pay additional fees for international application PCT/US2006/025201, dated Oct. 26, 2006.
PCT Invitation to Pay Additional Fees in International Application No. PCT/US2007/072209 dated Dec. 3, 2007.
Request for Continued Examination and Amendment for U.S. Appl. No. 11/731,568, filed Sep. 17, 2009.
Request for Continued Examination and Amendment, U.S. Appl. No. 11/064,156, 22 pages, dated Nov. 19, 2009.
Response to Extended European Search Report in European Application No. 10153350.3, filed Jun. 30, 2010.
Response to Non-Final Office Action, U.S. Appl. No. 11/042,912, (11 pgs.), dated Oct. 23, 2009.
Response to Office Action for European application 07842284.7. Filed Nov. 10, 2012.
Response to Office Action for European application 07842285.4. Filed Nov. 13, 2012.
Response to Office Action for European application 07842286.2. Filed Nov. 8, 2012.
Response to Office Action for European application 07842288.8. Filed Nov. 9, 2012.
Response to Office Action for European application 10153350.3. Filed Mar. 17, 2011.
Response to Office Action for U.S. Appl. No. 10/449,476, filed Aug. 12, 2009.
Response to Office Action for U.S. Appl. No. 10/449,503, filed Jul. 1, 2009.
Response to Office Action for U.S. Appl. No. 11/427,501, filed Jul. 1, 2009.
Response to Office Communication in European Application No. 10153350.3, filed Feb. 9, 2012.
Response to Official Letter for European application 07842284.7. Filed Oct. 14,2 011.
Response to Official Letter for European application 07842285.4. Filed Oct. 14,2 011.
Response to Official Letter for European application 07842286.2. Filed Oct. 14,2 011.
Response to Official Letter for European application 07842288.8. Filed Oct. 14,2 011.
Search Report and Written Opinion in International Application No. PCT/US2006/025201 dated Jan. 29, 2007.
Search Report and Written Opinion in International Application No. PCT/US2007/072217 dated Mar. 12, 2007.
Search Report in European Application No. 08158699.2 dated Aug. 2008.
State Intellectual Property Office of the People's Republic of China, Notification of the Second Office Action for Chinese Application No. 200880000182.5, dated Mar. 12, 2012.
State Intellectual Property Office of the People's Republic of China, Notification of the Third Office Action for Chinese Application No. 200680000182.5, dated Dec. 13, 2012.
State Intellectual Property Office of the People's Republic of China, Reexamination Decision for Chinese Application No. 200880000182 5, dated Nov. 20, 2013.
Taiwan Office Action, U.S. Appl. No. 94/102,179 (with English translation); 12 pages, dated May 13, 2010.
Trotty, "Technology (A Special Report)—The Wall Street Journal 2008 Technology Innovation Awards," The Wall Street Journal, Factiva. 2008.
International Preliminary Report on Patent ability in International Application No. PCT/US2005/002484 dated Aug. 3, 2006.
International Preliminary Report on Patentability for international application PCT/US2006/025201, dated Feb. 7, 2008.
International Preliminary Report on Patentability for international application PCT/US2007/072202. dated Jan. 15, 2009.
International Preliminary Report on Patentability for international application PCT/US2007/078204, dated Apr. 2, 2009.
International Preliminary Report on Patentability for international application PCT/US2007/078205, dated Mar. 26, 2009.
International Preliminary Report on Patentability for international application PCT/US2007/078207, dated Mar. 26, 2009.
International Preliminary Reporton Patentability for international application PCT/US2008/052943, dated Oct. 15, 2009.
International Preliminary Report on Patentability in International Application No. PCT/US/2007/072209, dated May 14, 2009.
International Preliminary Report on Patentability in International Application No. PCT/US/2008/050346, dated Jul. 23, 2009.
International Preliminary Report on Patentability in International Application No. PCT/US2007/072217 dated Feb. 12, 2009.
International Preliminary Report on Patentability in International Application No. PCT/US2007/078203, dated Mar. 26, 2009.
International Search Report and Written Opinion for international application PCT/US2007/078203, dated May 13, 2008.
International Search Report and Written Opinion for international application PCT/US2007/078204, dated May 15, 2008.
International Search Report and Written Opinion for international application PCT/US2007/078205, dated Sep. 11, 2007.
International Search Report and Written Opinion for international application PCT/US2007/078207, dated Apr. 7, 2008.
International Search Report and Written Opinion for international application PCT/US2008/0500346. dated May 22, 2008.
International Search Report and Written Opinion for international application PCT/US2008/050346 , dated May 22, 2008.
International Search Report and Written Opinion for International Patent Application No. PCT/US2007/072202, dated Mar. 25, 2008.
International Search Report and Written Opinion issued in PCT Application No. PCT/US2007/072209 dated Apr. 25, 2008.

(56) References Cited

OTHER PUBLICATIONS

International Search Report and Written Opinion issued in PCT Application No. PCT/US2007/072217 dated Mar. 31, 2008.
International Search Report and Written Opinion issued in PCT/US2014/028594, dated Jul. 28, 2014.
International Search Report and Written Opinion, PCT/US08/52943 8 pages, dated Sep. 26, 2008.
International Search Report for international application PCT/US2007/072209, dated Apr. 25, 2008.
Interview Summary dated Jul. 13, 2009 and Response to Interview Summary and Amendment filed Aug. 12, 2009, U.S. Appl. No. 11/190,331, 17 pages.
Interview Summary for U.S. Appl. No. 11/190,331, dated Jul. 13, 2009.
Japanese Office Action with English Transition; Application No. 2004-508670; PCT/US03/17203; pp. 7, dated Jan. 20, 2011.
Japanese Office Action, Application No. 2004-508669, (with English summary), (9 pages), dated Aug. 3, 2009.
Japanese Office Action, Application No. 2004-508670, (with English summary), (13 pages), dated Apr. 21, 2009.
Non-Final Office Action dated Apr. 1, 2009 and Response to Office Action filed Jul. 1, 2009, U.S. Appl. No. 10/449,503, 19 pages.
Non-Final Office Action dated Mar. 23, 2009 and Response to Office Action filed Jun. 22, 2009, U.S. Appl. No. 11/190,331, 61 pages.
Non-Final Office Action dated May 29, 2009 and Response to Office Action filed Aug. 12, 2009, U.S. Appl. No. 10/449,476, 20 pages.
Non-Final Office Action, U.S. Appl. No. 10/449,476, 6 pages, dated May 29, 2009.
Non-Final Office Action, U.S. Appl. No. 10/449,476, 8 pages, dated Oct. 29, 2008.
Non-Final Office Action, U.S. Appl. No. 10/987,051, 9 pages, dated Nov. 10, 2009.
Non-Final Office Action, U.S. Appl. No. 11/042,912, 8 pages, dated Jul. 23, 2009.
Non-Final Office Action, U.S. Appl. No. 12/259,745, 11 pages, dated Jul. 17, 2009.
Notice of Allowance dated Jun. 22, 2012 in U.S. Appl. No. 11/042,912.
Notice of Allowance dated Mar. 27, 2013 in U.S. Appl. No. 11/042,912.
Notice of Allowance dated Oct. 5, 2012 in U.S. Appl. No. 11/042,912.
Notice of Allowance in U.S. Appl. No. 11/042,912, dated Sep. 24, 2013.
Notice of Allowance in U.S. Appl. No. 11/253,467, dated Jun. 24, 2014.
Notice of Allowance in U.S. Appl. No. 11/380,340 dated Aug. 22, 2014.
Notice of Allowance in U.S. Appl. No. 11/619,390 dated Jul. 3, 2014.
Notice of Allowance in U.S. Appl. No. 11/619,390 dated Nov. 6, 2014.
Notice of Allowance in U.S. Appl. No. 11/620,927 dated Jun. 3, 2014.
Notice of Allowance in U.S. Appl. No. 11/853,678 dated Jul. 11, 2013.
Notice of Allowance in U.S. Appl. No. 11/853,678, dated Nov. 8, 2013.
Notice of Allowance in U.S. Appl. No. 11/853,678, dated Oct. 11, 2013.
Notice of Allowance in U.S. Appl. No. 11/853,701 dated Jul. 3, 2013.
Notice of Allowance in U.S. Appl. No. 11/853,701, dated Oct. 11, 2013.

* cited by examiner

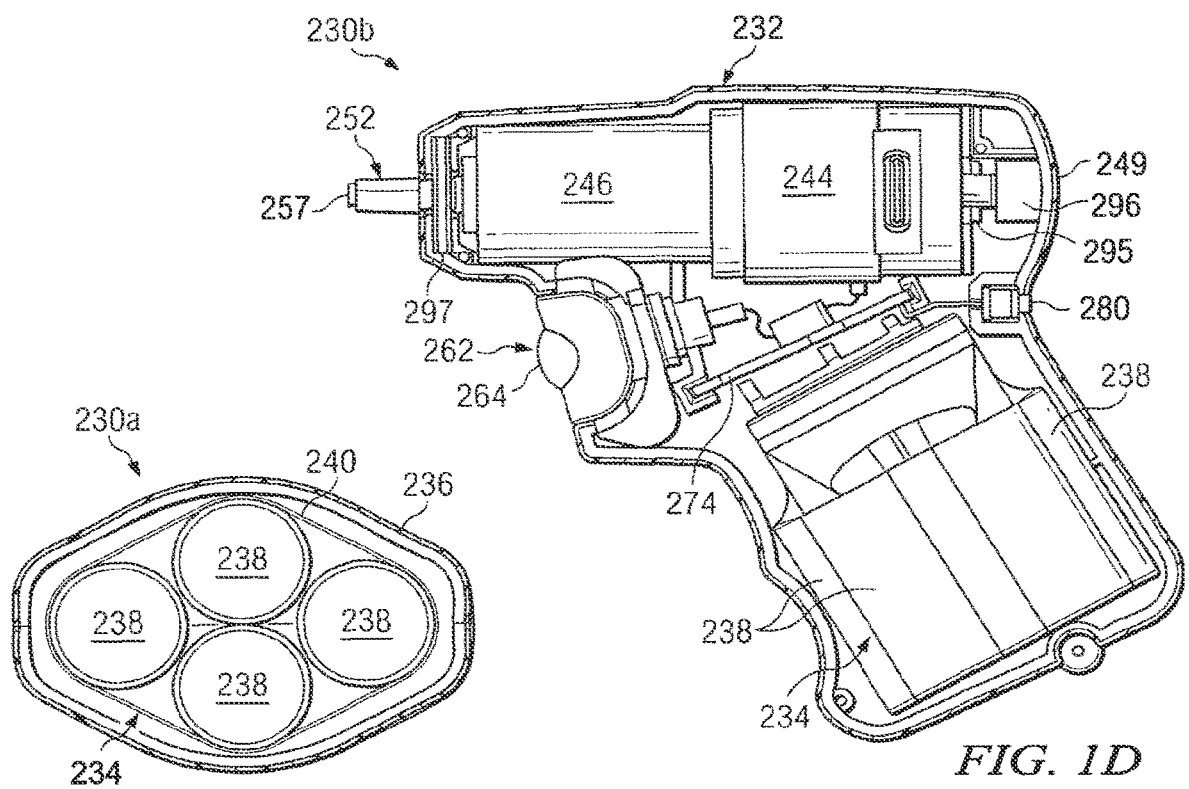
FIG. 1D
FIG. 1E
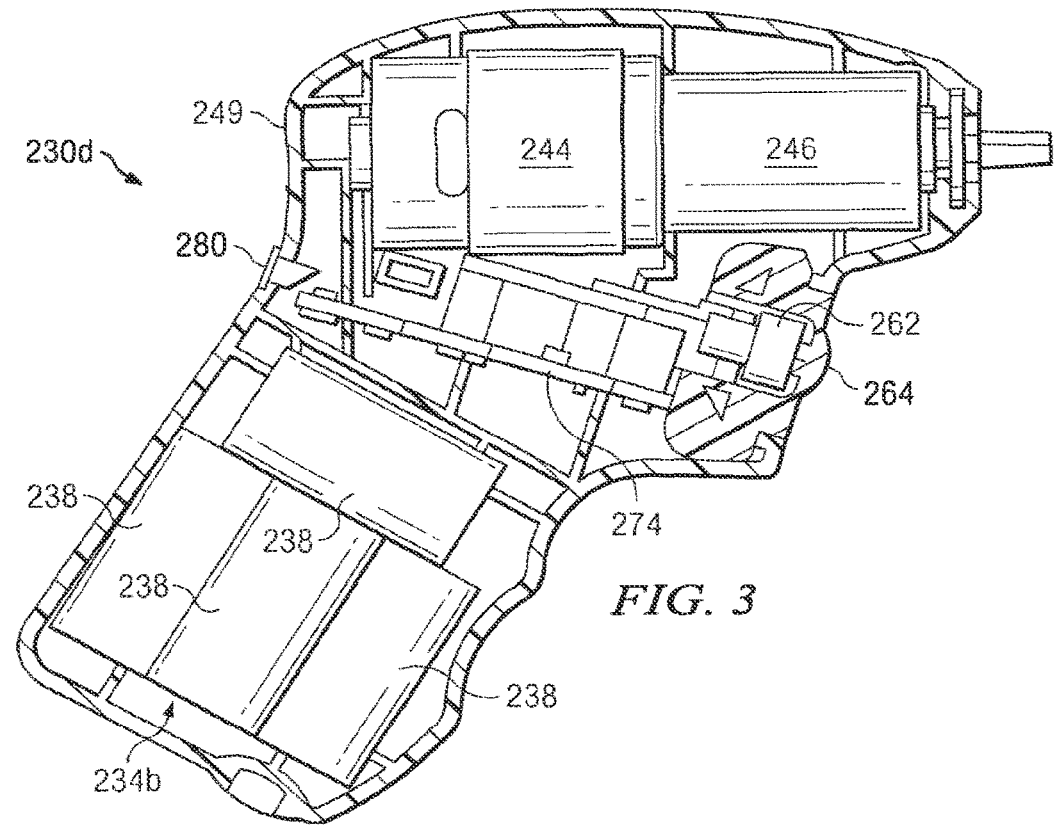
FIG. 3

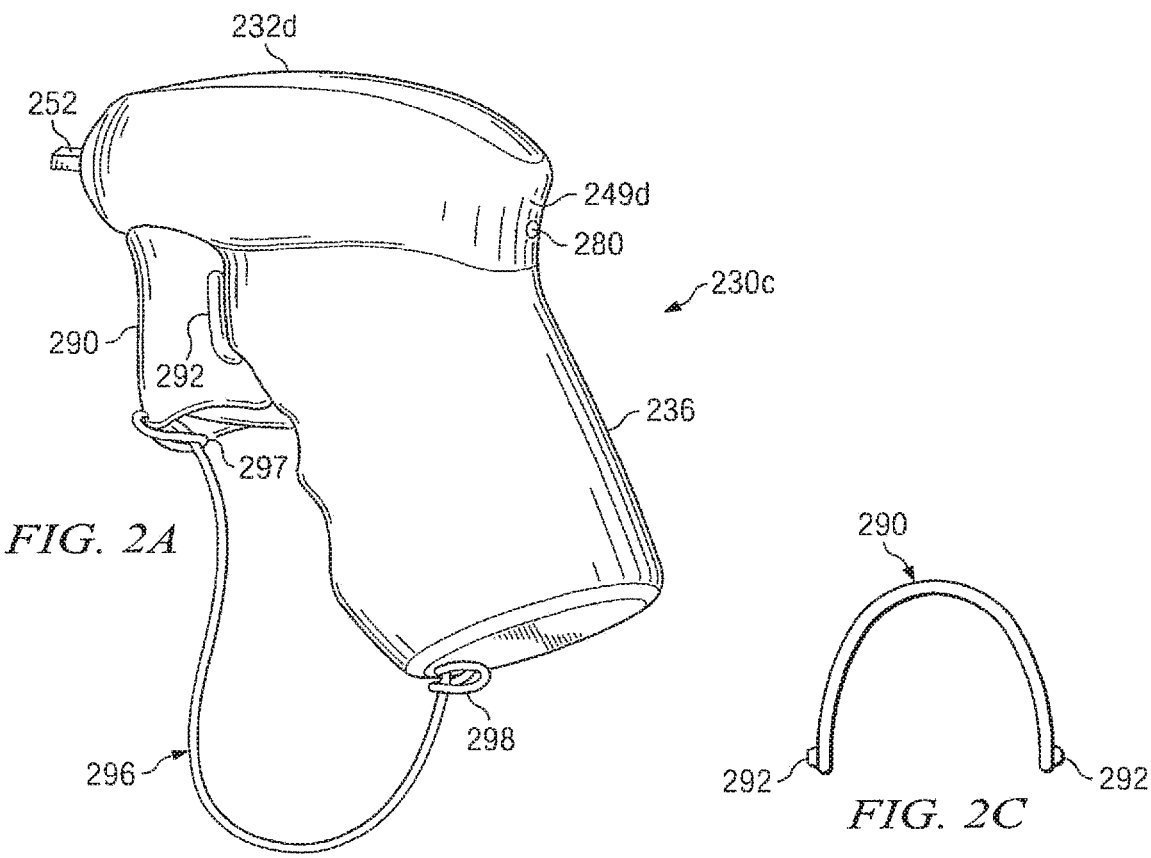
*FIG. 2A*
*FIG. 2C*
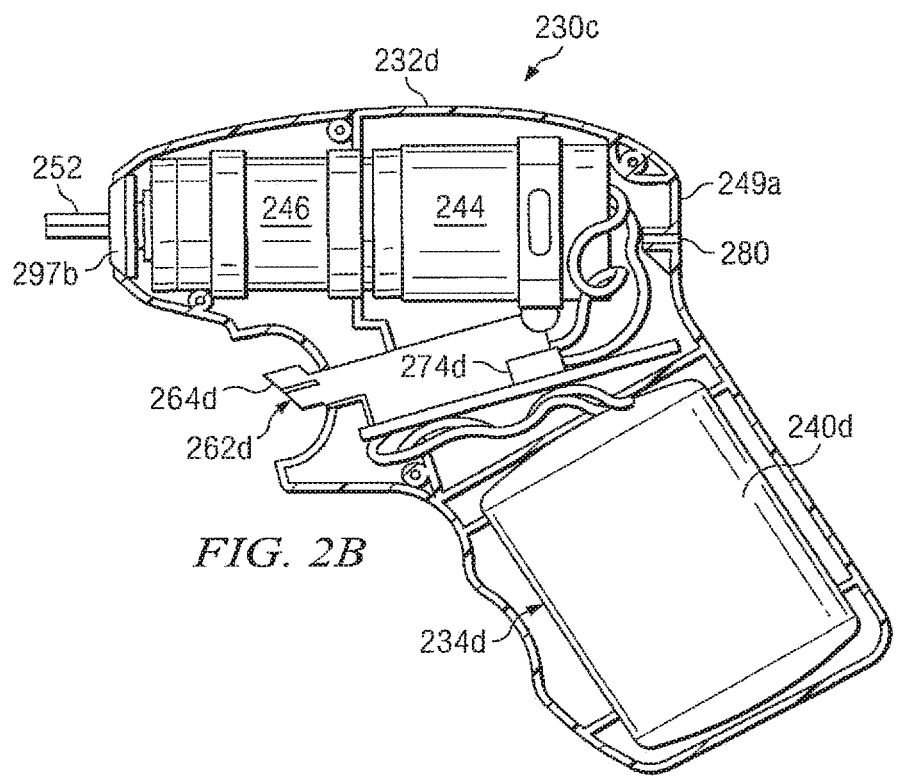
*FIG. 2B*

POWERED DRIVER

RELATED APPLICATION

This application is a continuation of pending patent application Ser. No. 13/609,001 entitled "Powered Driver," filed Sep. 10, 2012, which is a divisional of U.S. patent application Ser. No. 12/025,580 entitled "Powered Driver," filed Feb. 4, 2008, now U.S. Pat. No. 9,504,477, which claims priority to U.S. Provisional Patent Application Ser. No. 60/910,147, filed Apr. 4, 2007, and entitled "Powered Driver". The contents of U.S. patent application Ser. No. 10/449,476, filed May 30, 2003, now U.S. Pat. No. 7,699, 850; U.S. patent application Ser. No. 11/253,959, filed Oct. 19, 2005, now U.S. Pat. No. 8,506,568; U.S. patent application Ser. No. 11/253,467, filed Oct. 19, 2005, now U.S. Pat. No. 8,876,826; U.S. patent application Ser. No. 13/609, 001, filed Sep. 10, 2012; U.S. patent application Ser. No. 12/025,580, filed Feb. 4, 2008, now U.S. Pat. No. 9,504,477; and U.S. Provisional Patent Application No. 60/910,147, filed Apr. 4, 2007, are incorporated herein in their entirety by this reference.

STATEMENT OF GOVERNMENT INTEREST

Embodiments of present invention were developed using funds provided under United States Air Force contract number FA8650-06-C-6614. The U.S. government has certain rights in the invention.

TECHNICAL FIELD

The present disclosure is related to apparatus for penetrating a bone and associated bone marrow with a powered driver and inserting a intraosseous device into the bone marrow.

BACKGROUND OF THE DISCLOSURE

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

Obtaining satisfactorily vascular access may be a critical problem in approximately five (5%) percent to ten (10%) percent of patients treated in either prehospital or hospital settings. In the U.S. approximately six million patients annually may experience problems with traditional intravenous access. An essential element for treating medical emergencies is rapid establishment of an intravenous (IV) line to administer drugs and fluids directly into the circulatory system. Whether in an ambulance by paramedics, or in an emergency room by emergency specialists, the goal is the same—start an IV in order to administer life-saving drugs and fluids. To a large degree, the ability to successfully treat such critical emergencies is dependent on skill and luck of an operator in accomplishing vascular access.

While it is relatively easy to start an IV on many patients, doctors, nurses and paramedics often experience great difficulty establishing IV access in some patients. These patients are probed repeatedly with sharp needles in an attempt to solve this problem and may require an invasive procedure to finally establish an intravenous route. A further complicating factor in achieving IV access occurs "in the field" e.g. at the scene of an accident or during ambulance transport where it is difficult to see the target and excessive motion make accessing the venous system very difficult.

In the case of patients with chronic disease or the elderly, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

Powered drivers associated with intraosseous (IO) devices typically include a housing with various types of motors and/or gear assemblies disposed therein. A rotatable shaft may be disposed within the housing and connected with a gear assembly. Various types of fittings, connections, connectors and/or connector receptacles may be provided at one end of the rotatable shaft extending from the housing to releasably engage an IO device with the powered driver.

Examples of powered drivers are shown in pending patent applications Ser. No. 10/449,503 filed May 30, 2003 entitled "Apparatus and Method to Provide Emergency Access To Bone Marrow," now U.S. Pat. No. 7,670,328; Ser. No. 10/449,476 filed May 30, 2003 entitled "Apparatus and Method to Access Bone Marrow," now U.S. Pat. No. 7,699, 850; and Ser. No. 11/042,912 filed Jan. 25, 2005 entitled "Manual Intraosseous Device," now U.S. Pat. No. 8,641, 715.

SUMMARY OF THE DISCLOSURE

In accordance with teachings of the present disclosure, powered drivers are provided for use in gaining rapid access to a patient's vascular system. One embodiment may include a powered driver operable to insert an intraosseous device into a patient's bone marrow at a selected target site. The powered driver may include a power supply operable to make at least five hundred (500) insertions of an intraosseous device into bone and associated bone marrow. For some embodiments the associated power supply may be operable to make over one thousand (1000) insertions. For some applications a powered driver incorporating teachings of the present disclosure may have the general configuration of a small pistol.

One embodiment of the present disclosure may include providing emergency vascular access (EVA) by inserting a penetrator assembly into a bone and associated bone marrow by means of a powered driver, detaching the powered driver from the penetrator assembly, removing an inner penetrator from an outer penetrator of the penetrator assembly and attaching an adapter suitable to communicate medications or fluids with the bone marrow.

Another embodiment of the present disclosure may include manufacturing a powered driver, operable to penetrate bone and associated bone marrow, by forming a housing having a drive shaft extending from one end of the housing. A connector may be formed on the one end of the drive shaft to releasably attach a penetrator assembly to the drive shaft. A gear assembly may be disposed within the housing and rotatably engage with the drive shaft. A motor may be disposed within the housing and rotatably engaged to the gear assembly opposite from the drive shaft. A power supply and associated electrical circuitry operable to power the motor may also be disposed within the housing.

Powered drivers incorporating various teachings of the present disclosure may be used to provide intraosseous access to a patient's vascular system in the sternum, the proximal humerus (the shoulder area), the proximal tibia (below the knee) and the distal tibia (above the inside of the ankle).

A motor and gear assembly may be disposed within a housing and may be operable to rotate the drive shaft at approximately twelve hundred (1200) revolutions per minute (RPM). The gear assembly may reduce rotation speed of the motor by a ratio of approximately twenty to one (20:1). A trigger or on/off switch may extend from the housing. For some embodiments a five battery power pack may be disposed within the housing. For other embodiments a four battery power pack may be disposed within the housing. Some embodiments may include an over current fuse operational to reduce the chance of overheating of the batteries and/or power pack.

For some embodiments a powered drive may include a housing having a trigger operable to activate a motor disposed within the housing. A removable trigger guard may be disposed over the trigger when the powered driver is not in use. A lanyard may be used to securely engage the removable trigger guard with the housing. The length of the lanyard may be selected to accommodate placing the trigger guard over the trigger to prevent accidental activation and removing the trigger guard from covering the trigger to allow activation of the motor.

For some embodiments a powered driver may be provided with a housing having a motor and a gear assembly disposed therein. Sound dampening may be disposed within the housing to reduce noise associated with operation of the motor and gear assembly. A power supply status light may be provide at a proximal end of the housing indicate if the battery power is satisfactory (green light) or may be failing (red light). In one embodiment, the light will remain green so long as there is more than 10% of battery power remaining, once 90% of the battery power has been drained the light will turn red.

Another aspect of the present disclosure may include forming a sealed housing to prevent blood and/or other body fluids from contaminating interior portions of the housing and associated components such as the battery, motor and/or reduction gear assembly. A trigger mechanism or operating switch assembly may also be sealed with the housing to prevent contamination from blood and/or other fluids. Rubber or other elastomeric material may be used to from a flexible, fluid seal over the trigger mechanism or operating switch assembly.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 1D is a schematic drawing in section showing one example of a powered drive having sound dampening materials in accordance with teachings of the present disclosure;

FIG. 1E is a schematic drawing taken along lines 1E-1E of FIG. 1B showing one example of a four battery power supply having a generally diamond shaped cross section;

FIG. 2A is a schematic drawing showing an isometric view of a powered drive including a trigger guard and a lanyard attached thereto in accordance with teachings of the present disclosure;

FIG. 2B is a schematic drawing in section and in elevation showing a powered driver having a power source, a trigger, electrical circuits, a motor and a gear assembly incorporating various teachings of the present disclosure;

FIG. 2C is a schematic drawing showing a trigger guard in accordance with teachings of the present disclosure;

FIG. 3 is a schematic drawing in section and in elevation with portions broken away showing another example of a powered drive having a housing, trigger assembly, motor, reduction gear and power source incorporating teachings of the present disclosure;

DETAILED DESCRIPTION OF THE DISCLOSURE

Figure 1A:
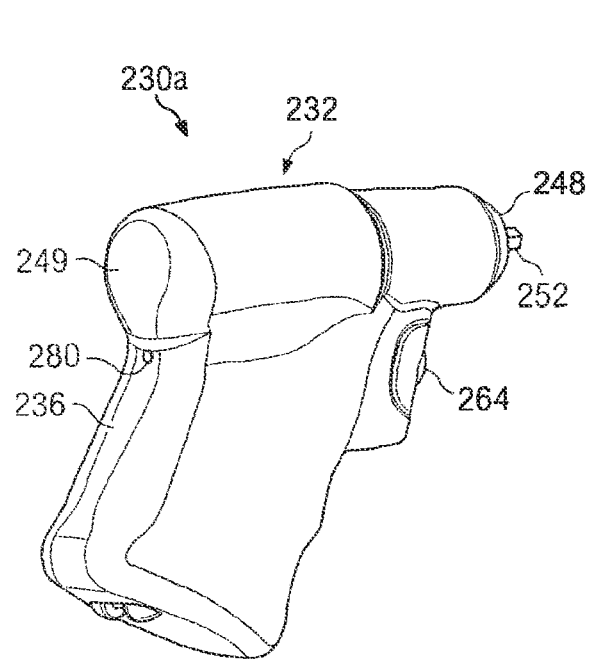
FIG. 1A is a schematic drawing showing an isometric view of one embodiment of a powered driver incorporating teachings of the present disclosure.
Figure 1B:
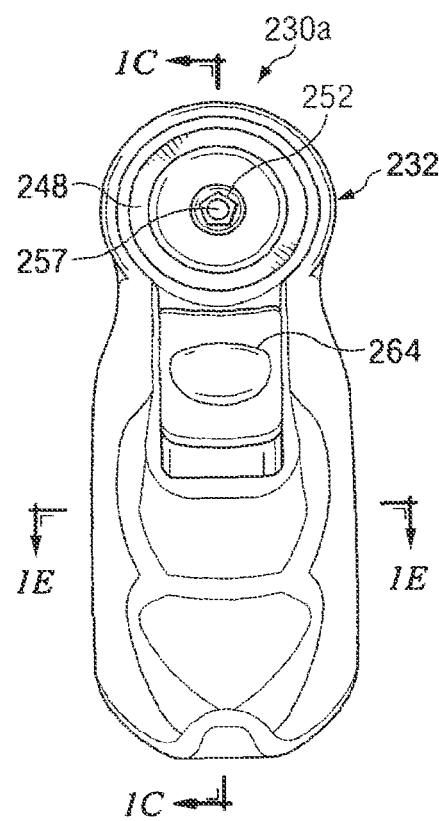
FIG. 1B is a schematic drawing showing a distal end view of the powered driver of FIG. 1A.

Preferred embodiments of the disclosure and its advantages may be best understood by reference to FIGS. 1A-5D wherein like numbers refer to same and like parts.

Vascular system access may be essential for treatment of many serious diseases, chronic conditions and acute emergency situations. Yet, many patients experience extreme difficulty obtaining effective treatment because of inability to obtain or maintain intravenous (IV) access. An intraosseous (IO) space provides a direct conduit to a patent's vascular system and systemic circulation. Therefore, IO access is generally an effective route to administer a wide variety of drugs, other medications and fluids equivalent to IV access. Rapid IO access or emergency vascular access (EVA) offers great promise for almost any serious emergency that requires vascular access to administer life saving drugs, other medications and/or fluids when traditional IV access is difficult or impossible.

Bone marrow typically includes blood, blood forming cells, and connective tissue disposed in an intraosseous space or cavity surrounded by compact bone. Long bones such as the tibia typically have an elongated central cavity filled with yellow bone marrow and adipose or connective tissue. Such cavities may also be referred to as a "medullary cavity", "bone marrow cavity" and/or "intraosseous space."

Compact bone disposed near an anterior or dorsal surface may be referred to as "anterior compact bone" or "anterior bone cortex." Compact bone disposed farther from the dorsal or anterior surface may be referred to as "posterior compact bone" or "posterior bone cortex."

The upper tibia proximate a patient's knee or the humeral head proximate a patient's shoulder may be used as insertion sites for an IO device to establish access with the patient's vascular system. Sternal access may also be used as an insertion site. Availability of multiple intraosseous insertion sites and associated target areas in adjacent bone marrow have proven to be especially important in applications such as emergency treatment of battlefield casualties or other mass casualty situations. Teachings of the present disclosure may be used to obtain intraosseous access at a wide variety of insertion sites and target areas.

IO access may be used as a "bridge" for temporary fluid and/or drug therapy during emergency conditions until conventional IV sites can be found and used. Conventional IV sites often become available because fluids and/or medication provided via IO access may stabilize a patient and expand veins and other portions of a patient's vascular system. IO devices and associated procedures incorporating teachings of the present disclosure may become standard care for administering medications and fluids in situations when IV access is difficult or not possible.

Intraosseous access may be used as a "routine" procedure with chronic conditions which substantially reduce or eliminate availability of conventional IV sites. Examples of such chronic conditions may include, but are not limited to, dialysis patients, patients in intensive care units and epilepsy patients. Intraosseous devices and associated apparatus incorporating teachings of the present disclosure may be quickly and safely used to provide IO access to a patient's vascular system in difficult cases such as status epilepticus to give medical personnel an opportunity to administer crucial medications and/or fluids. Further examples of such acute and chronic conditions are listed near the end of this written description.

Apparatus and methods incorporating teachings of the present disclosure may include using a first IO needle set having a fifteen (15) gage cannula with a length of approximately fifteen (15) millimeters to establish vascular access for patients weighing between approximately three (3) kilograms and thirty nine (39) kilograms. A second IO needle set having a fifteen (15) gage cannula with an approximate length of twenty-five (25) millimeters may be used to establish vascular access for patients weighing forty (40) kilograms and greater.

The term "driver" may be used in this application to include any type of powered driver satisfactory for inserting an intraosseous (IO) device such as a penetrator assembly, a catheter, an IO needle or an IO needle set into a selected portion of a patient's vascular system. Various techniques may be satisfactorily used to releasably engage or attach an IO device with a driver incorporating teachings of the present disclosure. A wide variety of connectors and associated connector receptacles, fittings and/or other types of connections with various dimensions and configurations may be satisfactorily used to releasably engage an IO device with a driver. A battery powered driver incorporating teachings of the present disclosure may be used to insert an intraosseous device into a selected target area in ten seconds or less. The reduced size and weight of drivers incorporating teachings of the present disclosure may accommodate use in emergency medical vehicles and emergency crash carts at medical facilities and/or carrying in backpacks of military personnel deployed for extended periods of time in remote locations.

The term "intraosseous (IO) device" may be used in this application to include any hollow needle, hollow drill bit, penetrator assembly, bone penetrator, catheter, cannula, trocar, inner penetrator, outer penetrator, IO needle or IO needle set operable to provide access to an intraosseous space or interior portions of a bone.

Figure 4A:
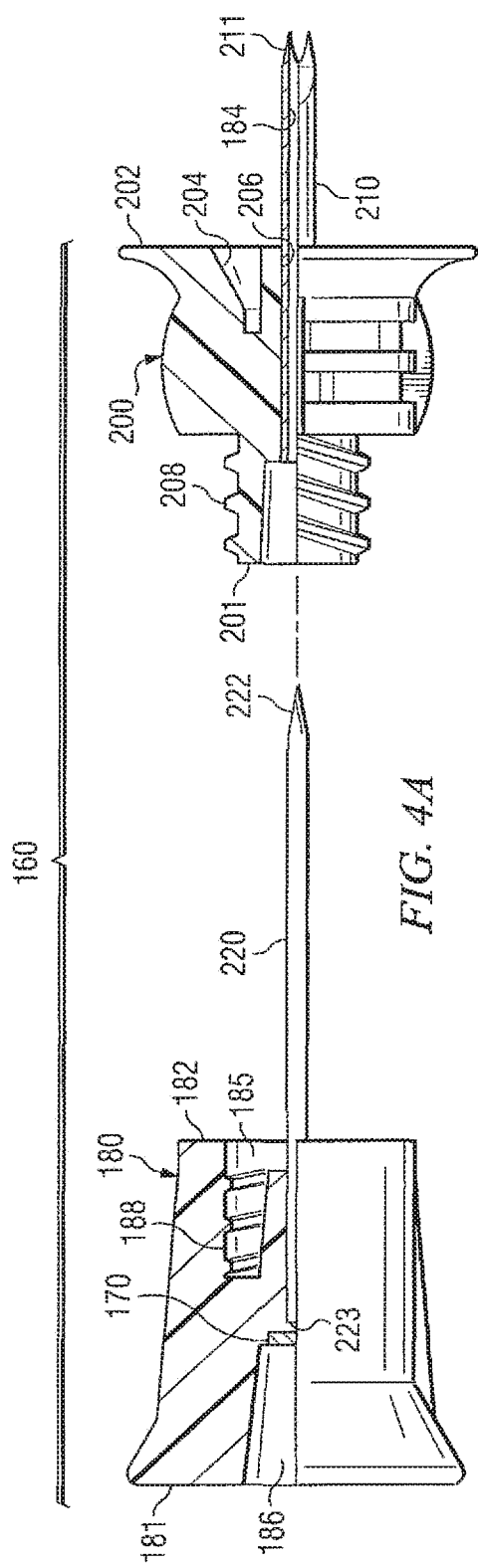
FIG. 4A is a schematic drawing showing one example of an intraosseous needle set or penetrator assembly which may be inserted into a patient's vascular system using a powered driver incorporating teachings of the present disclosure.
Figure 4B:
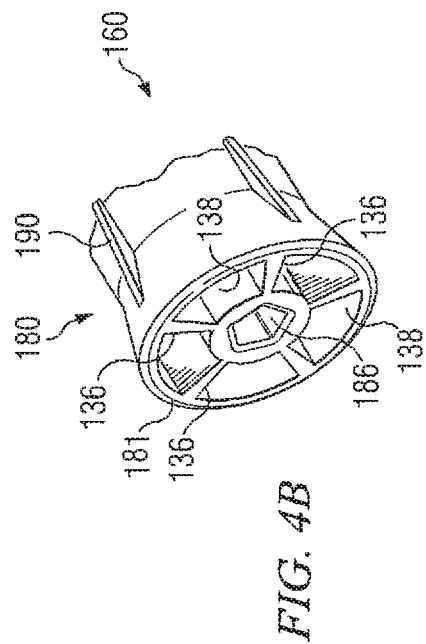
FIG. 4B is a schematic drawing showing an isometric view with portions broken away of a connector receptacle which may be releasably engaged with a powered driver incorporating teachings of the present disclosure.

For some applications an IO needle or IO needle set may include a connector with a trocar or stylet extending from a first one end of the connector. A second end of the connector may be operable to be releasably engaged with a powered driver incorporating teachings of the present disclosure. An IO needle or IO needle set may also include a hub with a hollow cannula or catheter extending from a first end of the hub. A second end of the hub may include an opening sized to allow inserting the trocar through the opening and the attached hollow cannula. The second end of the hub may be operable to be releasably engaged with the first end of the connector. As previously noted, the second end of the connector may be releasably engaged with a powered driver. A wide variety of connectors and hubs may be used with an IO device incorporating teaching of the present disclosure. The present disclosure is not limited to connector 180 or hub 200 as shown in FIGS. 4A and 4B.

Various features of the present disclosure may be described with respect to powered drivers 230a-230d, 330a and 330b (See FIG. 3). Various features of the present disclosure may also be described with respect to intraosseous device 160 such as shown in FIGS. 4A and 4B. However, the present disclosure is not limited to use with intraosseous device 160 or powered drivers 230a-230d, 330a and 330b.

Powered driver 230a as shown in FIGS. 1A, 1B, 1C, and 1E may be satisfactorily used to insert an intraosseous device at a desired insertion site adjacent to a bone and associated bone marrow. Powered driver 230a as shown in FIGS. 1A, 1B, 1C, and 1E may include one or more features of the present disclosure. At least one or more features of the present disclosure may also be shown with respect to powered drivers 230b, 230c, 230d, 330a, and 330b (See FIG. 3).

Powered driver 230a may include housing 232 having the general configuration of a small pistol defined in part by handle 236. Various components associated with powered driver 230a may be disposed within housing 232 including handle 236. For example a power source such as battery pack 234 may be disposed within handle 236. Battery pack 234 may have various configurations and may include multiple batteries 238 disposed within sealed packaging material 240 (See FIG. 1E). For purposes of describing various features of the present disclosure sealed packaging material 240 is not shown in FIGS. 1C, 1D and 2A.

Handle 236 may be generally described as an elongated, hollow container sized to receive battery pack or power supply 234 therein. Housing 230a including handle 236 may be formed from relatively strong, heavy duty polymeric material. For some applications housing 232 may be formed in two halves which are joined together to form a fluid tight seal with the various components associated with powered driver 230a disposed therein. For such applications power source or power supply 234 may include disposable batteries. In other embodiments, handle 236 may include exterior connections configured to allow recharging of power supply 234.

Motor 244 and gear assembly 246 may be disposed within portions of housing 232 adjacent to handle 236. For embodiments represented by powered drivers 230a-e, respective motor 244 and gear assembly 246 may be generally aligned with each other. Motor 244 may be rotatably engaged with one end of gear assembly 246. Drive shaft 250 may be rotatably engaged with and extend from another end of gear assembly 246 opposite from motor 244.

Distal end or first end 248 of housing 232 may include opening (not expressly shown) with portions of drive shaft 250 extending therefrom. For some applications end 252 of drive shaft 250 extending from housing 232 may have a generally pentagonal shaped cross section with tapered surfaces 256 disposed thereon. Tapered surfaces 256 may be disposed at an angle of approximately three (3.degree.) degrees with respect to a longitudinal axis or rotational axis (not expressly shown) associated with drive shaft 250. Relatively small magnet 257 disposed on the extreme end of drive shaft 250 opposite from distal end 248 of housing 232. Fittings and/or connectors with various dimensions and/or configurations other than end 252 of drive shaft 250 and/or magnet 257 may also be satisfactorily used with a powered driver incorporating teachings of the present disclosure.

Intraosseous devices having corresponding tapered openings or connector receptacles may be releasably engaged with end 252 of drive shaft 250 extending from housing 232. For example, end 252 extending from distal end 248 of housing 232 may be releasably engaged with tapered opening 186 in connector 180 as shown in FIGS. 4A and 4B. Tapered opening 186 and end 252 of drive shaft 250 preferably have non-sticking tapers.

For some applications both motor 244 and gear assembly 246 may have generally cylindrical configurations. Exterior portion 245 of motor 244 may correspond with the largest outside diameter or nominal outside diameter associated with motor 244. Exterior portion 247 of gear assembly 246 may correspond with the largest outside diameter or nominal outside diameter associated with gear assembly 246. For embodiments of the present disclosure represented by powered drivers 230a-230b, exterior portion 245 of motor 244 may have a nominal outside diameter portion larger than any outside diameter portion associated with gear assembly 246.

Portions of housing 232 may have generally similar cylindrical configurations corresponding with exterior portions of motor 244 and gear assembly 246. For example, segment 232a of housing 232 may have a generally cylindrical, hollow configuration with an inside diameter compatible with exterior portion 245 of motor 244. Housing segment 232b may have a generally cylindrical, hollow configuration with an inside diameter compatible with exterior portion 247 of gear assembly 246. Since portions of motor 244 have an outside diameter that is larger than the outside diameter of any portion of gear assembly 246, housing segment 32a may have a larger outside diameter than the outside diameter of housing segment 32b.

Motors and gear assemblies satisfactory for use with a powered driver incorporating teachings of the present disclosure may be obtained from various vendors. Such motor and gear assemblies are typically ordered as "sets" with one end of each motor securely attached to an adjacent end of an associated gear assembly. A drive shaft having various dimensions and/or configurations may extend from the gear assembly opposite from the motor. The gear assemblies may sometimes be referred to as "reduction gears" or "planetary gears". The dimensions and/or configurations of an associated housing may be modified to accommodate an associated motor and gear assembly.

Figure 1C:
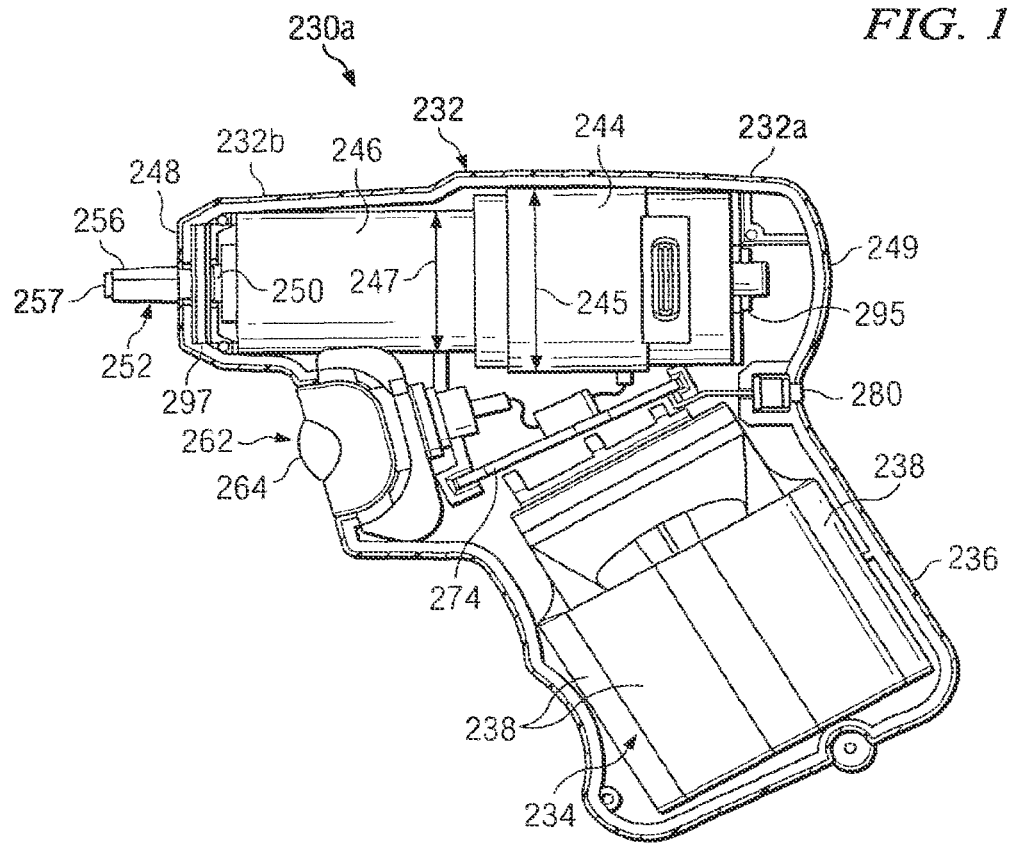
FIG. 1C is a schematic drawing in section and in elevation taken along lines 1C-1C OF FIG. 1B showing one example of a power supply incorporating teachings of the present disclosure.

For some applications a thrust pad structure 295 may be disposed between proximal end 249 of housing 232 and adjacent portions of motor 244. The thrust pad structure 297 may also be disposed adjacent to distal end 248 of housing 232. Thrust pad structures 295 and 297 may limit longitudinal movement of motor 244, gear assembly 246 and drive shaft 250 within associated portions of housing 232. Thrust pad structures 295 and 297 are also shown in FIGS. 1C and 1D. In some embodiments, thrust pad structure 295 may include one or more fixed portions of motor 244 configured to locate motor 244 in relation to housing 232.

For embodiments represented by power driver 230b as shown in FIG. 1D sound damping material 296 may be disposed adjacent to proximal end 249 of housing 232. One of the features of the present invention may include placing sound damping material at various locations within a housing to reduce noise associated with operating a powered driver while inserting an intraosseous device into a target area.

For embodiments of the present disclosure such as shown in FIG. 1D powered driver 230b may include electronic circuit board or smart board 274. Electrical circuit board 274 may also provide an electronic safety switch operable to turn off or deenergize motor 244 after power driver 230b has been energized for a selected amount of time. For example, electronic circuit board 274 may turn off power driver 230b after approximately ten seconds. For other applications, electronic circuit board 274 may turn off motor 244 after 20 seconds of operations. The time period for deenergizing motor 244 may be selected to save energy in an associated power source.

Powered drivers incorporating teaching of the present disclosure may typically run only a few seconds during insertion of an intraosseous device into bone and associated bone marrow. Activation of an associated motor for a longer period of time may imply a malfunction or use of the powered driver for other than normal IO insertion. To prevent draining of batteries, the timeout or timing circuit may automatically turn off the motor after a set time period such as ten (10) seconds or twenty (20) seconds. The time period may correspond with the length of time required to charge the capacitor shown in the above drawing. The timeout or timing circuit may function as a battery saving device. The timeout or timing circuit may be particularly important when a powered driver is carried in a tool box or a backpack to prevent accident draining of the battery.

Additional embodiments of the present disclosure are shown in FIGS. 2A, 2B, and 2C. For such embodiments trigger guard 290 may be releasably disposed over portions of trigger assembly 262d extending from housing 232d. Trigger guard 290 as shown in FIG. 2A may be formed from relatively strong but flexible material. Trigger guard 290 may have a generally U shaped configuration with ribs 292 formed on opposite sides of trigger guard 290. When trigger guard 290 is disposed over end or button 264d of trigger assembly 292d, ribs 292 will preferably be disposed immediately adjacent to portions of handle 236. A pair of ribs 292 disposed on opposite sides of trigger guard 290 may be used to easily release trigger guard 290 from covering trigger assembly 262d. By placing respective ribs 292 on opposite sides of trigger guard 290, either the thumb (not expressly shown) of an operator's left hand or right hand may be used to remove trigger guard 290.

Another aspect of the present disclosure may include attaching a trigger guard with a housing using a lanyard. For example, lanyard 296 as shown in FIG. 2A may be formed from various types of flexible, light weight material. First end 297 of lanyard 296 may be securely engaged with an appropriately sized opening formed in trigger guard 290. Second end 298 of lanyard 296 may be securely engaged on the end of handle 236. As a result of using lanyard 296, an operator may quickly release trigger guard 290 from power driver 230c but will avoid losing trigger guard 290.

As shown in FIG. 2A, power driver 230c may also include electrical circuit board 274d operable to activate light 280. Powered drive 230c as shown in FIGS. 1A-E, 2A-B, and 3 may include light 280 operable to indicate the status of power supply 240d disposed within handle 236. Light 280 may be disposed at proximal end or second end 249 of powered driver 230c. For some applications light 280 may be activated when button 264 of trigger assembly 262 is activated or depressed. A green light may be used to indicate that battery pack 234b has sufficient power to activate motor 244 and gear assembly 246. A red light may be visible at indicator 280 to indicate that battery power 234b may be failing. A wide variety of indicators including, but not limited to, light emitting diodes (LED's), liquid crystal displays (LCD's) and small more conventional light bulbs may be satisfactorily used with a powered driver according to teachings of the present disclosure. In some embodiments, indicators may be covered by a user's hand when in use to avoid visibility (e.g., in some military situations).

Additional embodiments of the present disclosure are shown in FIG. 3. For such embodiments a power supply 234b may include five batteries 238. The embodiment of the present disclosure as represented by powered driver 230c may also include one or more of the electronic circuit boards.

Penetrator assembly 160 as shown in FIGS. 4A and 4B may include connector 180, and associated hub 200, outer penetrator 210 and inner penetrator 220. Penetrator assembly 160 may include an outer penetrator such as a cannula, hollow tube or hollow drill bit and an inner penetrator such as a stylet or trocar. Various types of stylets and/or trocars may be disposed within an outer penetrator. For some applications outer penetrator or cannula 210 may be described as a generally elongated tube sized to receive inner penetrator or stylet 220 therein. Portions of inner penetrator 220 may be disposed within longitudinal passageway 184 extending through outer penetrator 210. The outside diameter of inner penetrator 220 and the inside diameter of longitudinal passageway 184 may be selected such that inner penetrator 220 may be slidably disposed within outer penetrator 210.

Metallic disc 170 may be disposed within opening 186 for use in releasably attaching connector 180 with magnet 257 disposed on end 252 of drive shaft 252. End 223 of inner penetrator 220 may be spaced from metallic disc 170 with insulating or electrically nonconductive material disposed therebetween.

Tip 211 of outer penetrator 210 and/or tip 222 of inner penetrator 220 may be operable to penetrate bone and associated bone marrow. The configuration of tips 211 and/or 222 may be selected to penetrate a bone or other body cavities with minimal trauma. First end or tip 222 of inner penetrator 220 may be trapezoid shaped and may include one or more cutting surfaces. In one embodiment outer penetrator 210 and inner penetrator 220 may be ground together as one unit during an associated manufacturing process. Providing a matching fit allows respective tips 211 and 222 to act as a single drilling unit which facilitates insertion and minimizes damage as portions of penetrator assembly 160 are inserted into a bone and associated bone marrow. Outer penetrator 210 and/or inner penetrator 220 may be formed from stainless steel, titanium or other materials of suitable strength and durability to penetrate bone.

Hub 200 may be used to stabilize penetrator assembly 160 during insertion of an associated penetrator into a patient's skin, soft tissue and adjacent bone at a selected insertion site. First end 201 of hub 200 may be operable for releasable engagement or attachment with associated connector 180. Second end 202 of hub 200 may have a size and configuration compatible with an associated insertion site for outer penetrator 210. The combination of hub 200 with outer penetrator 210 may sometimes be referred to as a "penetrator set" or intraosseous needle.

Connector 180 and attached inner penetrator 220 may be releasably engaged with each other by Luer type fittings, threaded connections or other suitable fittings formed on first end 201 of hub 200. Outer penetrator 210 extends from second end 202 of hub 200.

For some applications connector 180 may be described as a generally cylindrical tube defined in part by first end 181 and second end 182. The exterior of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. Longitudinal ridges 190 also allow connector 180 to be grasped for disengagement from hub 200 when outer penetrator 210 has been inserted into a bone and associated bone marrow.

Second end 182 of connector 180 may include opening 185 sized to receive first end 201 of hub 200 therein. Threads 188 may be formed in opening 185 adjacent to second end 182 of connector 180. Threaded fitting 188 may be used in releasably attaching connector 180 with threaded fitting 208 adjacent to first end 201 of hub 200.

First end 201 of hub 200 may include a threaded connector 208 or other suitable fittings formed on the exterior thereof. First end 201 may have a generally cylindrical pin type configuration compatible with releasably engaging second end or box end 182 of connector 180.

For some applications end 202 of hub 200 may have the general configuration of a flange. Angular slot or groove 204 sized to receive one end of protective cover or needle cap 234 may be formed in end 202. Slot or groove 204 may be used to releasable engage a needle cover (not expressly shown) with penetrator assembly 160.

For some applications a penetrator assembly may include only a single, hollow penetrator. For other applications a penetrator assembly may include an outer penetrator such as a cannula, hollow needle or hollow drill bit and an inner penetrator such as a stylet, trocar or other removable device disposed within the outer penetrator. Penetrator 210 is one example of a single, hollow penetrator or cannula.

The size of a penetrator may vary depending upon the intended application for the associated penetrator assembly. Penetrators may be relatively small for pediatric patients, medium size for adults and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient. Other configurations may be appropriate for bone and/or tissue biopsy.

For some applications connector 180 may be described as having a generally cylindrical configuration defined in part by first end 181 and second end 182. Exterior portions of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. Longitudinal ridges 190 also allow connector 180 to be grasped for disengagement from hub 200 when outer penetrator 210 has been inserted into a bone and associated bone marrow.

First end 181 of connector of 180 may included opening 186 sized to receive portions drive shaft 52 therein. A plurality of webs 136 may extend radially outward from connector receptacle 186. Webs 136 cooperate with each other to form a plurality of openings 138 adjacent to first end 181. Opening 186 and openings 138 cooperate with each other to form portions of a connector receptacle operable to receive respective portions of a connector (not expressly shown) therein.

FIG. 5A-5D show further examples of trigger guards which may be used with a powered driver in accordance with teachings of the present disclosure. Power drivers 330*a* and 330*b* may include cap 338 disposed on one end of handle 336. Cap 338 may be used to replace a power supply (not expressly shown) disposed within handle 336.

Figure 5A:
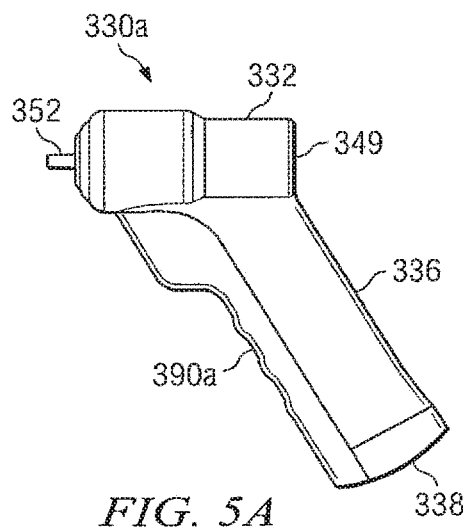
FIG. 5A is a schematic drawing in section with portions broken away showing one example of a protective cover in a first position blocking access to a trigger of a powered driver incorporating teachings of the present disclosure.
Figure 5B:
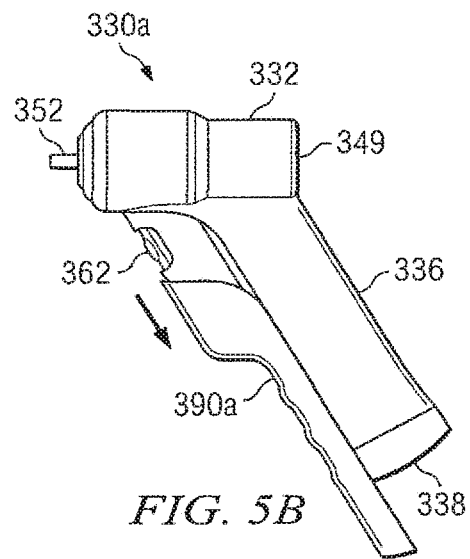
FIG. 5B is a schematic drawing showing the protective cover of FIG. 5A in a second position allowing access to the trigger of the powered driver.

For some embodiments a trigger guard may be slidably disposed on portions of a handle adjacent to an associated trigger assembly. For example, FIG. 5A shows power driver 330*a* with trigger guard 390*a* in its first position covering portions of trigger assembly 362. In FIG. 5B, trigger guard 390*a* is shown in its second position which allows access to trigger assembly 362 for operation of power driver 330*a*. For such embodiments, trigger guard 390*a* may be described as having a generally elongated configuration with a U shaped cross section. The profile of the U shaped cross section of trigger guard 390*a* may be selected to correspond with adjacent portions of handle 336 and trigger assembly 362. The length of trigger guard 390*a* may correspond approximately to the length of adjacent portion of handle 336.

Figure 5C:
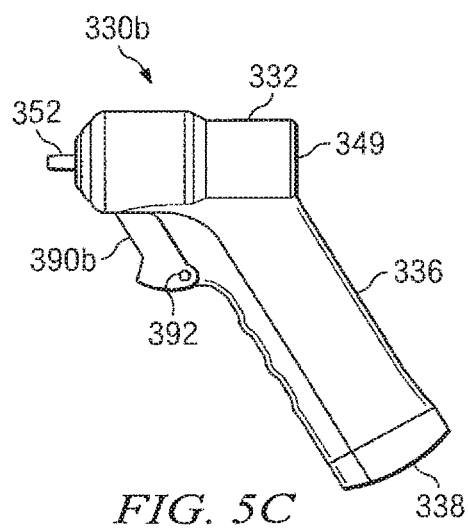
FIG. 5C is an isometric drawing showing another example of a trigger guard in a first position blocking access to a trigger of a powered driver incorporating teachings of the present disclosure.
Figure 5D:
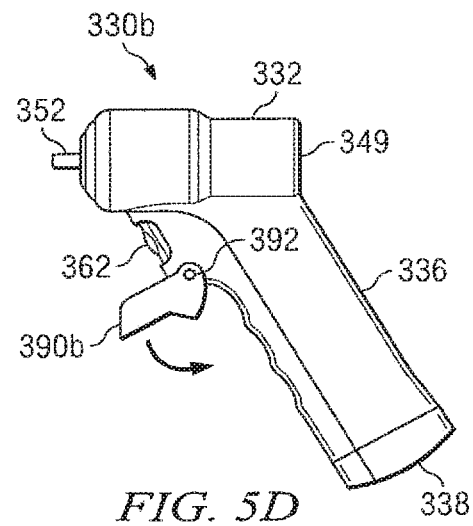
FIG. 5D is a schematic drawing showing the trigger guard of FIG. 5C in a second position allowing access to the trigger of the powered driver.

For embodiments represented by power driver 330*b* as shown in FIGS. 5C and 5D, trigger guard 390*b* may have a generally U shaped configuration similar to corresponding portions of trigger guard 390*a*. However, the length of trigger guard 390*b* may be substantially less than the length of trigger guard 390*a*. For embodiments such as shown in FIGS. 5C and 5D, pivot pin 392 may be disposed between portions of trigger guard 390*b* and adjacent portions of handle 396. Pivot pin 392 may allow rotational movement of trigger guard 390*b* from a first position blocking access to trigger assembly 362 as shown in FIG. 5C and a second position allowing access to trigger assembly 362 as shown in FIG. 5D.

Examples of acute and chronic conditions which may be treated using powered drivers, intraosseous devices, and procedures incorporating teachings of the present disclosure include, but are not limited to, the following:

Anaphylaxis (epinephrine, steroids, antihistamines, fluids, and life support)

Arrhythmia (anti-arrhythmics, electrolyte balance, life support);

Burns (fluid replacement, antibiotics, morphine for pain control);

Cardiac arrest (epinephrine, atropine, amiodarone, calcium, xylocaine, magnesium);

Congestive heart failure (life support, diuretics, morphine, nitroglycerin);

Dehydration (emergency port for life support, antibiotics, blood, electrolytes);

Diabetic Ketoacidosis (life support, electrolyte control, fluid replacement);

Dialysis (emergency port for life support, antibiotics, blood, electrolytes);

Drug overdose (naloxone, life support, electrolyte correction);

Emphysema (life support, beta adrenergics, steroids);

Hemophiliacs (life support, blood, fibrin products, analgesics);

Osteomyelitis (antibiotics directly into the site of infection, analgesics);

Pediatric applications (shock, dehydration, nutrition, electrolyte correction);

Renal Failure (both acute and chronic kidney failure, inability to purify blood);

Seizures (anti-seizure medications, life support, fluid balance);

Shock (life support fluids, pressor agents, antibiotics, steroids);

Sickle cell crisis (fluid, morphine for pain, blood, antibiotics); and

Trauma (emergency port for life support fluids, antibiotics, blood, electrolytes).

Although the present disclosure and its advantages have been described in detail, it should be understood that various changes, substitutions and alternations can be made herein without departing from the spirit and scope of the disclosure as defined by the following claims.

What is claimed is:

1. A method for providing intraosseous access, the method comprising:
   providing a driver and a penetrator assembly, the driver comprising:
      a housing having a proximal end, a distal end, a handle defining a hollow container, and an opening on the distal end of the housing;
      a motor disposed within a first segment of the housing;
      a power supply and associated electrical circuitry operable to power the motor, the power supply disposed within the hollow container of the handle;
      a trigger assembly operable to activate the motor;
      a gear assembly disposed within a second segment of the housing and engaged with the motor, the gear assembly being generally aligned with the motor; and
      a drive shaft rotatably engaged with the gear assembly and extending from an end of the gear assembly opposite from the motor, a portion of the drive shaft extending through the opening on the distal end of the housing;
   the penetrator assembly comprising:
      a connector having a first connector end, a second connector end, and a stylet extending from the second connector end, the first connector end including a connector receptacle, and the second connector end including a first connecting portion; and a hub having a first hub end, a second hub end, and a hollow cannula extending from the second hub end, the first hub end including a second connecting portion complementary to the first connecting portion on the second connector end of the connector, the first connecting portion of the connector configured to releasably engage the second connecting portion of the hub, and the hollow cannula configured to receive the stylet; and attaching the penetrator assembly to the driver by inserting the drive shaft of the driver into the connector receptacle of the connector;

inserting the penetrator assembly into a bone and associated bone marrow by means of the driver;

detaching the driver from the penetrator assembly by removing the drive shaft of the driver from the connector receptacle of the connector; and removing the stylet from the cannula of the penetrator assembly.

2. The method of claim 1, wherein the driver further comprises an electronic circuit board having an electronic safety switch configured to deenergize the motor after the motor has been energized for a selected amount of time.

3. The method of claim 1, wherein the driver further comprises an indicator light disposed at the proximal end of the housing and operable to indicate a status of the power supply.

4. The method of claim 1, wherein the power supply includes a battery.

5. The method of claim 4, wherein the battery is disposed within a sealed packaging material.

6. The method of claim 1, wherein the housing is formed from a heavy duty polymeric material.

7. The method of claim 1, wherein the portion of the drive shaft extending through the opening on the distal end of the housing includes a pentagonal shaped cross section.

8. The method of claim 1, wherein the portion of the drive shaft extending through the opening on the distal end of the housing includes a tapered surface.

9. The method of claim 8, wherein the tapered surface is disposed at an angle of approximately three degrees with respect to a longitudinal axis of the drive shaft.

10. The method of claim 1, wherein a tip end of the drive shaft opposite from the distal end of the housing includes a magnet.

11. The method of claim 1, wherein the motor and the gear assembly each have a generally cylindrical configuration.

12. The method of claim 11, wherein the first segment of the housing has a generally cylindrical hollow configuration with an inside diameter compatible with a corresponding exterior portion of the motor.

13. The method of claim 11, wherein the second segment of the housing has a generally cylindrical hollow configuration with an inside diameter compatible with a corresponding exterior portion of the gear assembly.

14. The method of claim 1, wherein an outside diameter of the first segment of the housing is larger than an outside diameter of the second segment of the housing.

15. The method of claim 1, wherein the driver further comprises a first thrust pad structure disposed between the proximal end of the housing and an adjacent portion of the motor, the first thrust pad structure including a fixed portion of the motor configured to locate the motor in relation to the housing.

16. The method of claim 15, wherein the driver further comprises a second thrust pad structure disposed adjacent to the distal end of the housing.

17. The method of claim 16, wherein the driver further comprises a sound damping material disposed adjacent to the proximal end of the housing and configured to reduce noise associated with operating the driver while inserting an intraosseous device into a target area.

* * * * *